(12) United States Patent
Jansen et al.

(10) Patent No.: US 7,208,270 B2
(45) Date of Patent: Apr. 24, 2007

(54) METHOD FOR DIAGNOSING A PERSON HAVING MULTIPLE SCLEROSIS

(75) Inventors: Burkhard Jansen, Laudongasse 69/39, 1080 Vienna (AT); Trevor Lucas, Kirchstettnergasse 3/9, 1160 Vienna (AT)

(73) Assignees: Burkhard Jansen, Vienna (AT); Trevor Lucas, Vienna (AT)

( * ) Notice: Subject to any disclaimer, the term of this patent is extended or adjusted under 35 U.S.C. 154(b) by 468 days.

(21) Appl. No.: 10/176,372

(22) Filed: Jun. 21, 2002

(65) Prior Publication Data

US 2003/0113752 A1    Jun. 19, 2003

Related U.S. Application Data

(60) Provisional application No. 60/299,765, filed on Jun. 22, 2001.

(51) Int. Cl.
*C12Q 1/68* (2006.01)
*G01N 33/53* (2006.01)
*C12P 19/34* (2006.01)

(52) U.S. Cl. .......................... 435/6; 435/7.1; 435/91.2
(58) Field of Classification Search ............... 435/6, 435/7.1, 91.2
See application file for complete search history.

(56) References Cited

U.S. PATENT DOCUMENTS

| 5,158,893 A | 10/1992 | Hackett et al. ............. 435/721 |
| 5,883,227 A | 3/1999 | Kline et al. ................. 530/350 |
| 6,822,072 B1 * | 11/2004 | Edwards et al. ............ 530/300 |

FOREIGN PATENT DOCUMENTS

WO        WO01/02860        1/2001

OTHER PUBLICATIONS

Database EMBL, Hypothetical Protein, Abstract XP-002227576, Database Accession No. AJ276469, Q9NY07 (2000).
Database EMBL, Uncharacterized Hypothalamus Protein HSMNP1, Abstract XP-002227577, Database Accession No. AK026642 (2000).
Database EMBL, Uncharacterized Hypothalamus Protein HSMNP1, Abstract XP-002227578, Database Accession No. AF220191, Q9NZ31 (2000).
Jacobsen et al. Nature Genetics 26: 495-499 (2000).
Mann et al. Neurology 54: 552-557 (2000).
Max et al. Neurology 54: 544-545 (2000).
Sawcer et al. Current Opinion in Immunology 10: 697-703 (1998).
Steckley et al. Neurology 54: 729-732 (2000).
Weinshenker et al. Neurology 54: 542-544 (2000).
Bastianello, Neurol Sci 22: S103-S107 (2001).
Capello et al., Neurol Sci 22: S113-S116 (2001).
Dyment et al., Human Molecular Genetics 6(10): 1693-1698 (1997).
Gasperini, Neurol Sci 22: S93-S97 (2001).
Poser et al., Clinical Neurology and Neurosurgery 103: 1-11 (2001).
Sadovnick et al., Clin Genet 56: 118-122 (1999).
Shi, Clinical Chemistry 47(2): 164-172 (2001).
Trojano et al., Neurol Sci 22: S98-S102 (2001).
Wen et al., Cancer Research 60: 2716-2722 (2000).

* cited by examiner

*Primary Examiner*—Kenneth R. Horlick
(74) *Attorney, Agent, or Firm*—Proskauer Rose LLP

(57) ABSTRACT

Described is a method for diagnosing a person having multiple sclerosis (MS) or being at risk of developing MS, comprising the following steps:
  providing a sample of a body fluid or tissue from said person, said sample containing at least one of the wild type SCF-Apoptosis-Response Gene- (wt-SARG-1-) protein and nucleic acids encoding wt-SARG-1, if taken from a person not having MS or a risk of aquiring MS,
  detecting the presence of wt-SARG-1-protein or nucleic acids encoding wt-SARG-1 in said sample and
diagnosing MS or a risk of aquiring MS, if wt-SARG-1-protein or nucleic acids encoding wt-SARG-1 are not present in said sample.

11 Claims, 23 Drawing Sheets

FIG. 4

>rSARG, 1037 bases
CCAGACTGGAAGCGAAGGCTGTGTTGCTGGGATGCCAGCTGCCGAGGGGC
TGCTTAAGCCTTGGCCCCCACTACTTTCTGTTTCAGCCCCACTTCTGTGC
GTGTCTTACTCCATTACCCCCAGGGGCTGACATGGACCCAAATCCACGAG
CAGCCCTGGAGCGGCAGCAGCTGCGTCTCAGGGAGCGGCAGAAGTTCTTC
GAGGACATTTTACAGCCAGAGACAGAGTTTGTTTTCCCCCTATCCCATCT
GCATCTCGAGTCACAAAGACCCCCCATAGGTAGCATCTCCTCGATGGAAG
TGAATGTGGACACACTGGAGCAGGTGGAATTTATTGACCTTGCGGATCAG
GATGGAGCAGATGTGTTCTTACCTTGTGAGGATTCTCCTCCAACTCCCCA
GAGGTCTGGAGTGGATGACCACCCAGAGGAGCTGAGCCTGCTGGTACCCA
CGTCAGACAGGACCACATCCCGGACCTCCTCCTTGTCCTCTGACTCCTCC
AACCTGCGCAGTCCAAATCCAAGTGATGGGGGAGGAGACACTCCCTTGGC
ACAGTCTGACGAGGAGGATGGGGACGGTGGAGGGGCAGAACCTGGACCTT
GCAGCTAGCAGAGGCCCCTTACAAACTGAGCGATCTGGCTGTTCTCCATG
GAGAGGAGACCTTAGGTCCACCAGAGCACTCTGGAGAAGACCTGACACTT
TACTTACATCAGCACCAAAGGGAGGGAAGGATGGTGGATGGTGTGCCTGA
GAGTTAGCCTCCCCGCTTTACTGATAACGCTGTCCTGCTGCCACGCCCCC
ACAGTGCTTTCTTCTGAGGTAGGACTTCCAAGTGAGACTCTCGAAGGTGA
GGTGGGACAAGATGCCACTGTTTTCTTACTCCCCTCCTGCCCCCAAATGA
TCCTGTAGTCTCCCACTAGTCTCCTAAGCCAGTGTCTCTGAGGGAAAGTT
CTGAGGAGTTCCACTTTGCAGTTATCCTGCCTCTATAAGTCCTTTCTGGG
AACAGGATATGGTATAAATAATAAATAATACTGTACC
>mSARG, 1029 bases
CCAGACCGGAAGCGAGGCTGTGTTGCTGGGATCCAACGCCGGCGCTGCTC
GCTCCCACGCCCCCGCCGCCGCTTGTCGGGAGCGCACCCAGGGAGCCAGC
GGGGCGCGGGCGCTGCAGGGGCTGACATGGACCCAAATCCGAGAGCAGCC
CTGGAGCGCCAACAGCTGCGGCTCCGGGAGAGGCAGAAGTTCTTTGAGGA
CATTTTACAGCCAGAGACAGAGTTTGTCTTCCCCCTGTCCCATCTGCACC
TGGAGTCACAAAGACCCCCCATAGGTAGCATCTCGTCTATGGAAGTGAAT
GTGGACACACTGGAGCAAGTGGAGTTTATTGATCTTGCGGATCAGGATGG
AGCAGATGTGTTCTTGCCTTGTGAGGAGTCCTCGCCAGCTCCCCAGATGT
CTGGAGTGGATGACCATCCAGAGGAGCTGAGCCTGCTGGTACCCACGTCT
GACAGGACCACATCCCGGACCTCCTCCTTGTCCTCTGACTCCTCCAACCT
GCGCAGTCCAAATCCAAGTGATGGGGGAGGAGACACTCCCTTGGCACAGT
CTGATGAGGAGGACGGGGATGACGGAGGGGCAGAGCCTGGACCCTGCAGC
TAGCAGTGGGCCTCGTACAGACTGACCAGCCCGGCTGTTCTCCATGGAAA
GGAGACCTAGGCCCAGCAGAGCCTGGAGAAGACCTGACACTTTCCTTACT
TCAGCACCAAAGGGAGGGAAGGATGGTGGATGGTGTGCCTGAGAGTTAGC
CTCCCCTGCTTTACCGTAACGCTATCCTGCTGCCACGCCCCCACAGTGCT
TTTCTTCTGAGGTAGGACTTCCAAGTGAGACTTGAGAGGTGAGGTGGGAC
AAGACGCAGCTGCTTTCTTAGTCCCCTCCTGCCCCCAGATGATCCTGTTG
TCTTCCACAGAGTCTCCTAAGCCAGTGTCTCTGAGGGGATGTTCTGAGGA
GTTCCACTTTCCAGTTATCCTGCCTCTATAAGTTCTTTTGGGAACAGGAT
ATGGTATAAATAATAAATAATAATATACC
>hSARG, 1062 bases
CCAGGCCGGAGCCAGGGGCCCCACTGTTGGGATGCTGGCTGCAGTGGGGC
GCCCCAAGCCCAGGTCCCCTCTGTCTTCTCTTTCGACTTTGCAGCTGTAC
TTGTTTTGCTCCTCTACCCGCAGGAGCTGACATGGACCCAAATCCTCGGG
CCGCCCTGGAGCGCCAGCAGCTCCGCCTTCGGGAGCGGCAAAAATTCTTC
GAGGACATTTTACAGCCAGAGACAGAGTTTGTCTTTCCTCTGTCCCATCT
GCATCTCGAGTCGCAGAGACCCCCCATAGGTATCTCATCCATGGAAG
TGAATGTGGACACACTGGAGCAAGTAGAACTTATTGACCTTGGGGACCCG
GATGCAGCAGATGTGTTCTTGCCTTGCGAAGATCCTCCACCAACCCCCCA
GTCGTCTGGGGTGGACAACCATTTGGAGGAGCTGAGCCTGCCGGTGCCTA
CATCAGACAGGACCACATCTAGGACCTCCTCCTCCTCCTCCGACTCC
TCCACCAACCTGCATAGCCCAAATCCAAGTGATGATGGAGCAGATACGCC
CTTGGCACAGTCGGATGAAGAGGAGGAAAGGGGTGATGCAGGGGCAGAGC
CTGGAGCCTGCAGCTAGCAGTGGGCCCTGCCTACAGACTGACCACGCTG
GCTATTCTCCACATGAGACCACAGGCCCAGCCAGAGCCTGTCGGGAGAAG
ACCAGACTCTTTACTTGCAGTAGGCACCAGAGGTGGGAAGGATGGTGGGA
TTGTGTACCTTTCTAAGAATTAACCCTCTCCTGCTTACTGCTAATTTTT
TCCTGCTGCAACCCTCCCACCAGTTTTTGGCTTACTCCTGAGATATGATT FIG. 4 (Fortsetzung)

```
TGCAAATGAGGAGAGAGAAGATGAGGTTGGACAAGATGCCACTGCTTTTC
TTAGCACTCTTCCCTCCCCTAAACCATCCCGTAGTCTTCTAATACAGTCT
CTCAGACAAGTGTCTCTAGATGGATGTGAACTCCTTAACTCATCAAGTAA
GGTGGTACTCAAGCCATGCTGCCTCCTTACATCCTTTTTGGAACAGAGCA
CGGTATAAATAATAAACTAATAATAATATGCC
```

FIG. 5

FIG. 5 (Fortsetzung)

CODING rSARG-coding
atggacccaaatccacgagcagccctggagcggcagcagctgcgtctcagggagcggcagaagttcttcgaggac
attttacagccagagacagagtttgttttcccccctatcccatctgcatctcgagtcacaaagacccccccataggt
agcatctcctcgatggaagtgaatgtggacacactggagcaggtggaatttattgaccttgcggatcaggatgga
gcagatgtgttcttaccttgtgaggattctcctccaactccccagaggtctggagtggatgaccacccagaggag
ctgagcctgctggtacccacgtcagacaggaccacatcccggacctcctccttgtcctctgactcctccaacctg
cgcagtccaaatccaagtgatgggggaggagacactcccttggcacagtctgacgaggaggatggggacggtgga
ggggcagaacctggaccttgcagctag
477bp MDPNPRAALERQQLRLRERQKFFEDILQPETEFVFPLSHLHLESQRPPIGSISSMEVNVDTLEQVEFIDLADQDG
ADVFLPCEDSPPTPQRSGVDDHPEELSLLVPTSDRTTSRTSSLSSDSSNLRSPNPSDGGGDTPLAQSDEEDGDGG
GAEPGPCS
158 amino acids mSARG-coding
ATGGACCCAAATCCGAGAGCAGCCCTGGAGCGCCAACAGCTGCGGCTCCGGGAGAGGCAGAAGTTCTTT
GAGGACATTTTACAGCCAGAGACAGAGTTTGTCTTCCCCCTGTCCCATCTGCACCTGGAGTCACAAAGA
CCCCCCATAGGTAGCATCTCGTCTATGGAAGTGAATGTGGACACACTGGAGCAAGTGGAGTTTATTGAT
CTTGCGGATCAGGATGGAGCAGATGTGTTCTTGCCTTGTGAGGAGTCCTCGCCAGCTCCCCAGATGTCT
GGAGTGGATGACCATCCAGAGGAGCTGAGCCTGCTGGTACCCACGTCTGACAGGACCACATCCCGGACC
TCCTCCTTGTCCTCTGACTCCTCCAACCTGCGCAGTCCAAATCCAAGTGATGGGGAGGAGACACTCCC
TTGGCACAGTCTGATGAGGAGGACGGGGATGACGGAGGGGCAGAGCCTGGACCCTGCAGCTAG
477bp MDPNPRAALERQQLRLRERQKFFEDILQPETEFVFPLSHLHLESQRPPIGSISSMEVNVDTLEQVEFIDLADQDG
ADVFLPCEESSPAPQMSGVDDHPEELSLLVPTSDRTTSRTSSLSSDSSNLRSPNPSDGGGDTPLAQSDEEDGDDG
GAEPGPCS
158 amino acids hSARG-coding
ATGGACCCAAATCCTCGGGCCGCCCTGGAGCGCCAGCAGCTCCGCCTTCGGGAGCGGCAAAAATTCTTCGAGGAC
ATTTTACAGCCAGAGACAGAGTTTGTCTTTCCTCTGTCCCATCTGCATCTCGAGTCGCAGAGACCCCCCATAGGT
AGTATCTCATCCATGGAAGTGAATGTGGACACACTGGAGCAAGTAGAACTTATTGACCTTGGGGACCCGGATGCA
GCAGATGTGTTCTTGCCTTGCGAAGATCCTCCACCAACCCCCCAGTCGTCTGGGGTGGACAACCATTTGGAGGAG
CTGAGCCTGCCGGTGCCTACATCAGACAGGACCACATCTAGGACCTCCTCCTCCTCCTCCGACTCCTCCACC
AACCTGCATAGCCCAAATCCAAGTGATGATGGAGCAGATACGCCCTTGGCACAGTCGGATGAAGAGGAGGAAAGG
GGTGATGGACGGGCAGAGCCTGGAGCCTGCAGCTAG
486bp MDPNPRAALERQQLRLRERQKFFEDILQPETEFVFPLSHLHLESQRPPIGSISSMEVNVDTLEQVELIDLGDPDA
ADVFLPCEDPPPTPQSSGVDNHLEELSLPVPTSDRTTSRTSSSSSSDSSTNLHSPNPSDDGADTPLAQSDEEEER
GDGGAEPGACS
161 amino acids

FIG. 6

```
rSARG-coding    1  ATGGACCCAAATCCACGAGCAGCCCTGGAGCGGCAGCAGCTGCGTCTCAGGGAGCGGCAG
mSARG-coding    1  ATGGACCCAAATCCGAGAGCAGCCCTGGAGCGCCAACAGCTGCGGCTCCGGGAGAGGCAG
hSARG-coding    1  ATGGACCCAAATCCTGGGCCCCCCTGGAGCGCCAGCAGCTCCGCCTTTGGGAGCGGCAA rSARG-coding   61  AAGTTCTTCGAGGACATTTTTACAGCCAGAGACAGAGTTTGTTTTCCCCCTATCCCATCTG
mSARG-coding   61  AAGTTCTTTGAGGACATTTTTACAGCCAGAGACAGAGTTTGTCTTCCCCCTGTCCCATCTG
hSARG-coding   61  AAATTCTTCGAGGACATTTTTACAGCCAGAGACAGAGTTTGTCTTTCCTCTGTCCCATCTG rSARG-coding  121  CATCTCGAGTCACAAAGACCCCCCATAGGTAGCATCTCGTCGATGGAAGTGAATGTGGAC
mSARG-coding  121  CACCTGGAGTCACAAAGACCCCCCATAGGTAGCATCTCGTCTATGGAAGTGAATGTGGAC
hSARG-coding  121  CATCTCGAGTCGCAGAGACCCCCCATAGGTAGTATCTCATCCATGGAAGTGAATGTGGAC rSARG-coding  181  ACACTGGAGCAGGTGGAATTTATTGACCTTGCGGATCAGGATGGAGCAGATGTCTTCTTA
mSARG-coding  181  ACACTGGAGCAAGTGGAGTTTATTGATCTTGCGGATCAGGATGGAGCAGATGTGTTCTTG
hSARG-coding  181  ACACTGGAGCAAGTAGAACTTATTGACCTTGGTGACCCGGATGCAGCAGATGTGTTCTTC rSARG-coding  241  CCTTGTCAGGCATTCTCCTCCAACTCCCCAGAGGTCTGGAGTGGATGACCCACCAGAGGAG
mSARG-coding  241  CCTTGTCAGGCGTCCTGGCCAGCTCCCCAGATGTCTGGAGTGGATGACCATCCAGAGGAG
hSARG-coding  241  CCTTGCGAAGATCCTCCACCAACCCCCAGTCGTCTGGGGTGGACAACCATTGGAGGAG rSARG-coding  301  CTGAGCCTGCTGGTACCCACGTCAGCAGGACCACATCCCGGACCTCCTCCTTGTCCTCT
mSARG-coding  301  CTGAGCCTGCTGGTACCCACGTCTGACAGGACCACATCCCGACCTCCTCCTTGTCCTCT
hSARG-coding  301  CTGAGCCTGCCGGTGCCTACATCAGACAGGACCACATCTAGGACCTCCTCCTCCTCCTCC rSARG-coding  361  ---GACTCCTCCA----ACCTGCGCAGTCCAAATCCAGTGATGGGGGAGGAGACACTCCC
mSARG-coding  361  ---GACTCCTCCA----ACCTGCGCAGTCCAAATCCAGTGATGGGGGAGGAGACACTCCC
hSARG-coding  361  TCCGACTCCTCCACCAACCTGCATAGCCCAAATCCAGTGATGATGGAGCAGATACCCCC rSARG-coding  415  TTGGCACAGTC---TGACGAGGAGGATGGGGACGGTGGAGGGGCAGAACCTGGACCTTGC
mSARG-coding  415  TTGGCACAGTC---TGATGAGGAGGACGGCCATCGCGGAGGGGCAGAGCCTGGACCCTGC
hSARG-coding  421  TTGGCACAGTCGGATGAAGAGGAGGAAAGCGGTGATGGAGGGGCAGAGCCTGGAGCCTGC rSARG-coding  472  AGCTAG
mSARG-coding  472  AGCTAG
hSARG-coding  481  AGCTAG
```

FIG. 7

```
rSARG-coding    1   MDPNPRAALERQQLRLRERQKFFEDILQPETEFVFPLSHLHLESQRPPIGSISSMEVNVD
mSARG-coding    1   MDPNPRAALERQQLRLRERQKFFEDILQPETEFVFPLSHLHLESQRPPIGSISSMEVNVD
hSARG-coding    1   MDPNPRAALERQQLRLRERQKFFEDILQPETEFVFPLSHLHLESQRPPIGSISSMEVNVD rSARG-coding   61   TLEQVEFIDLADQDGADVFLPCEDSPPTPGRSGVDDHPEELSLLVPTSDRTTSRTSSLSS
mSARG-coding   61   TLEQVEFIDLADQDGADVFLPCEESSAPQMSGVDDHPEELSLLVPTSDRTTSRTSSLSS
hSARG-coding   61   TLEQVEFIDLGPPDAADVFLPCEDPPPTPQSSGVDNHLEELSLPVPTSDRTTSRTSSSSS rSARG-coding  121   -DS-SNLRSPNFSDGGGDTPLAQSDEED--SDGEGAEPGFCS
mSARG-coding  121   -DS-SNLRSPNFSDGGGDTPLAQSDEED--SDDGGAEPGFCS
hSARG-coding  121   SDSSTNLHSPNFSDDSADTPLAQSDEEERSD-EGAEPGACS
```

FIG. 8 t→c point mutation in a familial multiple sclerosis patient at nucleotide 67 of coding sequence. Substitution of phenylanaline (F) for leucine (L) at amino acid 23.

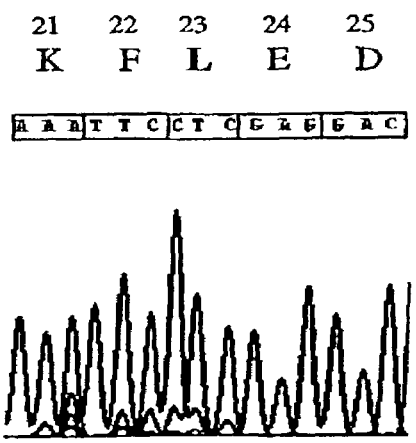

```
Wild type    1   MDPNPRAALERQQLRLRERQKFFEDILQPETEFVFPLSHLHLESQRPPIGSISSMEVNVD   60
Mutattion    1   MDPNPRAALERQQLRLRERQKFLEDILQPETEFVFPLSHLHLESQRPPIGSISSMEVNVD   60

Wild type   61   TLEQVELIDLGDPDAADVFLPCEDPPPTPQSSGVDNHLEELSLPVPTSDRTTSRTSSSSS  120
Mutation    61   TLEQVELIDLGGPDAADVFLPCEDPPPTPQSSGVDNHLEELSLPVPTSDRTTSRTSSSSS  119

Wild type  121   SDSSTNLHSPNPSDDGADTPLAQSDEEEERGDGGAEPGACS  161
Mutation   120   SDSSTNLHSPNPSDDGADTPLAQSDEEEERGDGGAEPGACS  160
```

FIG. 15 c→t point mutation in a familial multiple sclerosis patient at nucleotide 359 of coding sequence. Substitution of Phenylanaline (F) for serine (S) at amino acid 120

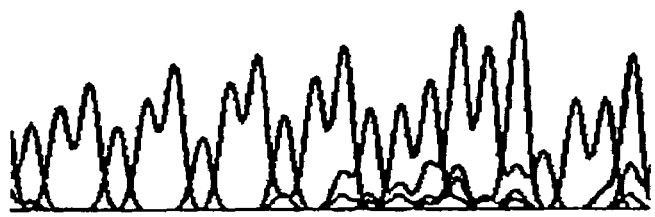

```
Wild type   1  MDPNPRAALERQQLRLRERQKFFEDILQPETEEVFPLSHLHLESQRPPIGSISSMEVNVD  60
Mutattion   1  MDPNPRAALERQQLRLRERQKFFEDILQPETEFVPPLSHLHLESQRPPIGSISSMEVNVD  60

Wild type  61  TLEQVELIDLGDPDAADVFLPCEDPPPTPQSSGVDNHLEELSLPVPTSDRTTSRTSSSSS  120
Mutation   61  TLEQVELIDLGDPDAADVFLPCEDPPPTPQSSGVDNHLEELSLPVPTSDRTTSRTSSSSF  119

Wild type 121  SDSSTNLHSPNPSDDGADTPLAQSDEEEERGDGGAEPGACS  161
Mutation  120  SDSSTNLHSPNPSDDGADTPLAQSDEEEERGDGGAEPGACS  160
```

FIG. 16 a→g point mutation in a familial multiple sclerosis patient at nucleotide 89 of coding sequence. Substitution of glycine (G) for glutamic acid (E) at amino acid 30.

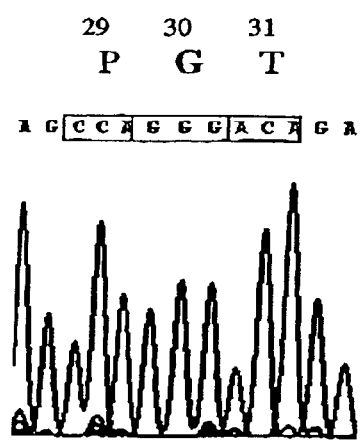

```
Wild type   1  MDPNPRAALERQQLRLRERQKFFEDILQPETEFVFPLSHLHLESQRPPIGSISSMEVNVD  60
Mutattion   1  MDPNPRAALERQQLRLRERQKFLEDILQPGTEFVFPLSHLHLESQRPPIGSISSMEVNVD  60

Wild type  61  TLEQVELIDLGDPDAADVFLPCEDPPPTPQSSGVDNHLEELSLPVPTSDRTTSRTSSSSS 120
Mutation   61  TLEQVELIDLGGPDAADVFLPCEDPPPTPQSSGVDNHLEELSLPVPTSDRTTSRTSSSSS 119

Wild type 121  SDSSTNLHSPNPSDDGADTPLAQSDEEEERGDGGAEPGACS 161
Mutation  120  SDSSTNLHSPNPSDDGADTPLAQSDEEEERGDGGAEPGACS 160
```

FIG. 17

Deletion of codon in familial multiple sclerosis patient. Loss of serine residue

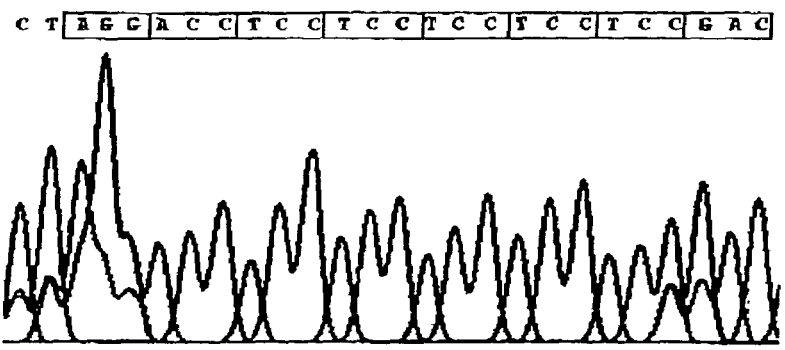

```
Wild type   1  MDPNPRAALERQQLRLRERQKFFEDILQPETEFVFPLSHLHLESQRPPIGSISSMEVNVD  60
Mutattion   1  MDPNPRAALERQQLRLRERQKFFEDILQPETEFVFPLSHLHLESQRPPIGSISSMEVNVD  60

Wild type  61  TLEQVELIDLGDPDAADVFLPCEDPPPTPQSSGVDNHLEELSLPVPTSDRTTSRTSSSSS 120
Mutation   61  TLEQVELIDLGDPDAADVFLPCEDPPPTPQSSGVDNHLEELSLPVPTSDRTTSRT-SSSS 119

Wild type 121  SDSSTNLHSPNPSDDGADTPLAQSDEEEERGDGGAEPGACS 161
Mutation  120  SDSSTNLHSPNPSDDGADTPLAQSDEEEERGDGGAEPGACS 160
```

SARG INTRON/EXON STRUCTURE

Transcription start site initiator consensus YYCARR is underlined
Donor (GU) and acceptor (AG) splice sites are underlined in italics
Exons are in bold type
Coding exon sequences are in italics EXON 1
<u>CCAGG</u>CCGGAGCCAGGGGCCCCACTGTTGGGATGCTGGCTGCAGTGGGGCGCCCCAAGCCCAGGT
CCCCTCTGTCTTCTCTTTCGACTTTGCAGCTGTACTTGTTTTGCTCCTCTACCCGCAGGAGCTGA
C
+1
ATGGACCCAAATCCTCGGGCCGCCCTGGAGCGCCAGCAGCTCCGCCTTCGGGAGCGGCAAAAATT
CTTCGAGGACATTTTACAGCCAGAGACAGAGTTTGTCTTTCCTCTGTCCCATCTGCATCTCGAGT
CGCAGAGAC
+139
INTRON 1
<u>*GT*</u>AAGTCCCAAGTCCTGAGAAGAGGGACTGGGGTAGGGTAGGGA
GGATGTCCTGTGGGTCCTGAATCTTGTGGCACTCTCTCCCCTCTGGTTTT
CTTGGCCCTCTATGCTTCTAACTTGGGACCTGACATGTAACTCTCACTGT
CCTGGTGTGCAGCTTGGGTCCTCCTGACTTGCCCACTTCTTGATCCGC<u>*AG*</u>
EXON 2
+139
CCCCCATAGGTAGTATCTCATCCATGGAAGTGAATGTGGACACACTGGAGCAAGTAGAACTTATT
GACCTTGGGGACCCGGATGCAGCAGATGTGTTCTTGCCTTGCGAAGATCCTCCACCAACCCCCCA
GTCGTCTG
+276
INTRON 2
<u>*GT*</u>ATGCCCCTCTGCTTTGGGGACTTCAGTGCCAGTCAGCCAGAGCCGGATGTCAGGCTCTGA
AACGAGGCTACAAGGCTGGGCTGGGGAAGTACACAAGTAAGGGCTGGAAG
TGGGTGTTTCTACCAATGAAACAGCTGCCTGTTCTGATTTTAGGGAAGTT
GACCCTGAGGGAGAACTGGGTTACACATCTCTAATCCAAAATTCTGGGAA
CGGTCAATCTCTTCTTTAATTTTACATTTGTTATATTAATATAATTAGTC
ACTATAATTAAAATAATGTAAAATTGTAATTTTTATATTTGGCAACTTAA
GTAGTTTTAGTCATTATAATGATATTAATATGTATTGAGTACTTTAGTAG
GTTCCAATACTGTACTAAAGTACTTTACATATATTATCTCAATCCTTACA

METHOD FOR DIAGNOSING A PERSON HAVING MULTIPLE SCLEROSIS

This application claims priority to U.S. Ser. No. 60/299,765, filed Jun. 22, 2001, the entirety of which is hereby incorporated by reference.

The invention relates to a method for diagnosing a person having multiple sclerosis (MS) or being at risk of developing MS. Further, the invention relates to a method for diagnosing a person having cancer or being at risk of acquiring cancer.

Multiple sclerosis (MS) is a common demyelinating disease of the central nervous system (CNS) affecting up to 0.1% of the north European caucasian population and is considered an auto-immune syndrome directed against unidentified central nervous tissue antigens. The determination of susceptibility to MS development is complex and governed by both environmental and genetic factors (Ebers et al, 1995; Sawcer and Goodfellow, 1998; Sadovnick et al, 2000) with approximately 20% of patients having one or more affected relatives (Chataway et al, 1998). Although thought to be a polygenetic disease, candidate gene approaches have been adopted to isolate genes linked to MS (Weinshenker and Kantarci, 2000). Association with the Caucasian haplotype DRB*1501-DQA*0102-DQB1*0602 (Haines et al, 1998) and a point mutation in the protein tyrosine phosphatase receptor-type C (Jacobsen et al, 2000) have been linked to some cases. Recently, the importance of apoptosis in both T cell elimination and damage to neurons and oligodendrocytes in MS have been recognised (reviewed in Zipp, 2000).

However, to date no clear marker has been reported, although at least a portion of MS cases are clearly familial inherited. A mere recognition of MS or even providing a risk association would be very beneficial for early onset of therapy or preventive measures.

It is therefore an object of the present invention to provide an efficient diagnosis system for MS giving a clear indication and a clear correlation to this disease.

The subject matter of the invention is therefore a method for diagnosing a person having multiple sclerosis (MS) or being at risk of developing MS, characterised by the following steps:
  providing a sample of a body fluid or a tissue from said person, said sample containing at least one of the wild type SCF-Apoptosis-Response Gene 1- (wt-SARG-1-) protein and nucleic acids encoding wt-SARG-1, if taken from a person not having MS or a risk of aquiring MS,
  detecting the presence of wt-SARG-1-protein or nucleic acids encoding wt-SARG-1 in said sample and
  diagnosing MS or a risk of aquiring MS, if wt-SARG-1-protein or nucleic acids encoding wt-SARG-1 are not present in said sample.

Surprisingly, SARG-1 protein turned out to be a very specific marker for MS. Persons having either mutated SARG-1 protein or not expressing any SARG-1 protein due to mutations in SARG-1, have a clearly enhanced risk of MS. Investigations on the immuno-histochemical localisation of SARG-1 protein indicated that this protein is located in the grey and white matter of the CNS. The role of SARG-1 in apoptotic induction prompted a candidate gene approach to analyse the mutational status of SARG-1 in cases of familial MS. Indeed, DNA from 20 unrelated familial MS patients was examined by PCR amplification and DNA-sequencing of the SARG-1 locus and compared to SARG-1 sequences from healthy controls. It was found that all control samples demonstrated wild-type SARG-1 genomic sequences whereas in DNA from MS patients only 6 from 20 DNA samples were even able to be amplified by PCR, i.e. 14 from 20 did not show any detectable SARG-1 signals. In 4 of the 6 other patients genetic alterations were seen. A T→C point mutation at nucleotide 67 resulting in a substitution of phenylalanine with leucine at amino acid 23 (numbering of amino acids and nucleotides according to FIGS. 4–8); a C→T point mutation at nucleotide 359 resulting in the substitution of phenylalanine for serine at amino acid 120 (FIG. 16), A→G point mutation a nucleotide 89 resulting in the substitution of glycine for glutamic acid at amino acid 30 (FIG. 17), deletion of a codon between amino acid 116 and 121 resulting in the loss of a serine residue (FIG. 18). Sequencing of only 20 control DNA samples revealed only wild-type sequence.

Surprisingly, it was also observed that changes in wild type SARG-1 or SARG-1 protein was seen in several cancer cells. In sequence analysis of over 30 cancer cells, a G residue is always present at position 280 resulting in a leucine residue at position 94 instead of a valine (A nucleotide) or methionine (T nucleotide). In a human melanoma cell line two mutations in SARG-1 are found: A→G point mutation at nucleotide 74 resulting in the substitution of aspartic acid for glycine and a C→T point mutation at nucleotide 289 resulting in the substitution of histidine for thyrosine at amino acid 97.

There is a number of restriction sites involved in these mutations: T→C at nucleotide 67 creates a number of restriction sites: Eco88I, XhoI, PaeR7I, Sfr274I, Ama781I, BcoI, BsoBI, AvaI; C→T at nucleotide 359 creates an additional BseRI restriction-site.

Therefore, a further object of the present invention relates to a method for diagnosing a person having cancer or being at risk of aquiring cancer, characterised by the following steps:
  providing a sample of a body fluid or tissue from said person, said sample containing at least one of the wt SARG-1 protein and nucleic acids encoding wt-SARG-1, if taken from a person not having cancer or being at risk of aquiring cancer,
  detecting the presence of wt-SARG-1 protein or nucleic acids encoding wt-SARG-1 in said sample and
  diagnosing cancer or a risk of aquiring cancer, if wt-SARG-1 protein or nucleic acids encoding wt-SARG-1 are not present in said sample.

The source of the sample is always dependent on the nature of the cancer or disease to be diagnosed. Especially preferred samples according to the present invention are derived from human blood, plasma, serum, lymph, nerve-cell.containing tissue, cerebrospinal fluid, all biopsy-material, including tumor tissue, bone marrow, nervous tissue, skin, hair, tears, fetal material including amniocentesis material, uterine tissue, saliva, faeces, sperm, etc.

In principle, any method for detecting the presence of wt-SARQ-1 protein or nucleic acid encoding wt-SARG-1 in the sample may be applied according to the present invention. Preferably methods are applied which allow also a characterisation of specific SARG-1 mutants if present, either by giving the information that a mutant is present or by analysing the nature of the mutant form in detail.

Especially detecting the presence of point mutations may be preferred within the present invention, i.e. non-wt-forms of SARG-1 differing from wt-SARG-1 or wt-SARG-1 protein in one nucleic acid residue, or one amino acid residue, respectively. The method according to the present invention may be designed to identify those point mutations, especially point mutations leading to the different amino acid sequence, e.g. exchange of one amino acid residue from the wild type SARG-1 protein.

Suitable methods for detecting the presence of wt-SARG-1 protein or nucleic acids encoding are known in the art, preferably nucleic acids encoding wt-SARG-1 are detected by nucleic acid amplification methods, especially polymerase chain reaction methods, single-strand conformation polymorphism (SSCP) analysis, restriction analysis, microarray technology, proteomics, etc. These methods have been shown as being fast, highly reliable and easily conductable on a high throughput basis. Those tests could be performed on standard tissue or body fluid samples, such as blood, hair or saliva.

On the other hand, preferred methods for detecting the presence of wt-SARG-1 protein encompass the application of a wt-SARG-1 protein antibody, especially a monoclonal antibody, e.g. in a ELISA-format. Such antibodies may be easily produced on an industrial scale with a high degree of standardisation potential.

The method according to the present invention is especially suited to be applied within a screening test format.

The SARG-1 intron/exon structure is given in FIG. 19. The transcription start site initiator consensus YYCARR is underlined. Donor (GU) and acceptor (AG) splice sites are underlined in italics; exons are in bold type. Coding exon sequences are in italic. SARG-1 is located on human chromosome 20q12-13.12.

The present invention also relates to a further aspect, to a nucleic acid molecule comprising a sequence according to Seq.ID.No. 1 (FIG. 4) encoding human wild-type SARG-1. Such nucleic acids may be used for diagnosis but also for therapeutic aspects by providing therapeutic molecules or gene sequences for gene therapy aspects, e.g. by antisense strategies, design of small molecule drugs.

The present invention also encompasses nucleic acid molecules comprising a sequence according to Seq.ID.No. 1, wherein one nucleic acid residue is exchanged by a different nucleic acid residue (e.g. T is replaced by C, G or A) wherein said exchange preferably results in a different SARG-1-protein amino acid sequence.

Especially preferred exchanges are selected from a T to C exchange at position 67 of Seq.ID.No. 1, an A to G exchange at position 74 of Seq.ID.No. 1, an A to G exchange at position 89 of Seq.ID.No. 1, a C to T exchange at position 289 of Seq.ID.No. 1 and a C to T exchange at position 359 of Seq.ID.No. 1. These exchanges relate to exchanges already observed in MS patients or cancer cells. Further exchanges resulting in a viable phenotype are also preferred.

Other preferred mutations in the nucleic acid molecule according to the present invention comprises a deletion in the coding region, preferably a deletion of one or more codons (e.g. 3 nucleic acids, or 6, 9, 12, etc.). One of these mutations leads to the deletion of a codon between amino acids 116 and 121, resulting in the loss of a serine residue (FIG. 19). Mutations leading to non-functional SARG-1 on SARG-1 protein may also be located in the controlling regions (5' or 3') and/or in the sequences, especially at critical positions for correct splicing.

When the nucleic acid molecule according to the present invention is used for a diagnostic purpose, it is not necessary to use the whole sequence. For use as a probe or performing a method according to the present invention a fragment of Seq.ID.No. 1, preferably having a length of at least 12, more preferred at least 15, especially at least 20, nucleic acid residues is suitable for performing various tests, especially diagnostic tests with these probes, e.g. as a probe to identify or isolate nucleic acid samples or even chromosomal samples or as PCR primers, etc.

The nucleic acid molecules according to the present invention are not restricted to the coding sequence according to Seq.ID.No. 1, but also relate to the genomic counterparts including the whole-exon/intron-structure of this gene, especially also imitations in the non-coding-region resulting in non-wild type forms of the protein (or non-translated forms of the protein) are encompassed by the present invention.

The present invention also relates to a polypeptide being encoded by this nucleic acid molecule, e.g. comprising an amino acid sequence according to Seq.ID.No. 2. There is single potential N-gly-cosylation site with consensus Asn-X-Ser/Thr (amino acid residues 131-133)

MDPNPRAALERQQLRLRERQKFFEDILQPETEFVFPLSHLHLESQRPPIG

SISSMEVNVDTLEQVELIDLGDPDAADVFLPCEDPPPTPQSSGVDNHLEE

LSLPVPTSDRTTSRTSSSSSSDSSTNLHSPNPSDDGADTPLAQSDEEEER

GDGGAEPGACS

All threonine and serine residues may be O-glycosylated. Computer predictions indicate high likelihood of glycosylation of serine residues 91, 108, 113, 117, 118, 119, 120, 121, 123, 124 and 133 and the threonine residues 88, 107, 111, 112, 115 and 125.

Similarly, all threonine and serine residues may be phosphorylated. Computer predictions indicate high likelihood of phosphorylation of serine residues 54, 92, 108, 113, 116, 117, 118, 119, 120, 121, 123, 124, 129, 133 and 144 and the threonine residues 61, 88, 107, 112 and 139.

No signal sequences, characteristic domains or other 3-dimensional structures have been detected other than potential protein kinase recognition sites. Of course, also amino acid sequences also having an amino acid residue exchange or a deletion are also encompassed by the present invention.

Amino acid residue exchanges of the polypeptide according to the present invention are preferably selected from amino acid residues Phe23, Asp25, Glu30, His97 and Ser120, especially Phe23 to Leu 23, Asp25, to Gly25, Glu30 to Gly30, His97 to Tyr97 and Ser120 to Phe120 exchanges.

The present invention provides SARG-1 mutant forms as specific markers for (acute) myeloid leukaemia or other leukaemia subtypes as described hereinafter. Deletions of the SARG-1 gene may be partial or full to serve as marker. Diagnostic tests for screening for the presence or absence of such a marker are easily conceivable and reduced to practice by the skilled man in the art.

Preferred polypeptides according to the present invention are re-combinantly produced which exhibit structural differences compared to wt-SARG-1 protein, e.g. differential glycosylation, especially non-homogeneous glycosylation.

The present invention also relates to a method for making an antibody preparation comprising administering a polypeptide according to the present invention to an animal, allowing said animal to generate antibodies against said polypeptide, extracting antibody-containing body fluids or tissue from said animal and preparing an antibody preparation against said polypeptide from said body fluids or tissue. This method is especially applicable for making polyclonal antibodies.

For making monoclonal antibodies a method for making such an antibody preparation is preferred, comprising administering a polypeptide according to the present invention to an animal, allowing said animal to generate antibodies against said polypeptide, removing the spleen of said animal, preparing fusion cells of said spleen cells with suitable hybridoma generating cells, generating hybridoma cells producing monoclonal antibodies against said polypeptide, cloning and culturing said hybridoma cells, thereby expressing moncolonal antibodies, and preparation of said monoclonal antibodies. The skilled man in the art thereby relies on methods readily available for such purposes and e.g. described in "Antibodies: A laboratory manual" by Ed Harlow, Cold Spring Harbor Laboratory; David Lane, Imperial Cancer Research Fund Laboratories, 1988. Of course, also phage display peptides may also easily be generated.

The present also relates to a kit for performing the in vitro diagnosing method according to the present invention which comprises at least means for detecting the presence of wt-SARG-1 protein or nucleic acids encoding wt-SARG-1. The skilled man in the art can envisage the basis of the disclosure of the present application a wide number of suitable alternatives, e.g. anti-wt-SARG-1 protein antibodies, nucleic acid probes selectively binding to wt-SARG-1, nucleic acid primers defining a region being selective for a wt-SARG-1, a chip comprising said nucleic acid probes or said nucleic acid primers. Other preferred means or assays are assays in which proteins bind to SARG-1 such as antibodies or peptides including mutation specific antibodies, ELISAS, Western Blotting assays, flow cytometry assays and assays using immunohistochemical techniques including confocal microscopy.

A further aspect of the present invention relates to a transgenic non-human animal model of the present invention, especially an animal wherein the SARG-1 gene has been mutated or knocked out. A SARG-1 knock out mouse is especially preferred. Methods for providing such models, especially the mouse models, are readily available to the skilled man in the art. Such an animal model is extremely useful in studying genetic variations and mutations of SARG-1, especially with respect to its MS-related disorders.

The term "transgenic" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

Transgenic animals fall into two groups, colloquially termed "knockouts" and "knockins". In the present invention, knockouts have a partial or complete loss of function in one or both alleles of the endogenous SARG-1. Knockins have an introduced transgene with altered genetic sequence and function from the endogenous gene. The two may be combined, such that the naturally occurring gene is disabled, and an altered form introduced.

In a knockout, preferably the target gene expression is undetectable or insignificant. A knock-out of a SARG-1 means that function of the SARG-1 protein has been substantially decreased so that expression is not detectable or only present at insignificant levels or mutated according to the teachings according to the present invention to perform as suitable model for the situation in humans as described herein. This may be achieved by a variety of mechanisms, including introduction of a mutation or disruption of the coding sequence, e.g. insertion of one or more stop codons, insertion of a DNA fragment, etc., deletion of coding sequence, substitution of stop codons for coding sequence, etc. In some cases the exogenous transgene sequences are ultimately deleted from the genome, leaving a net change to the native sequence. Different approaches may be used to achieve the "knock-out". A chromosomal deletion of all or part of the native gene may be induced, including deletions of the non-coding regions, particularly the promoter region, 3' regulatory sequences, enhancers, or deletions of genes that activate expression of SARG-1. A functional knock-out may also be achieved by the introduction of an anti-sense construct that blocks expression of the native genes (for example, see Li and Cohen (1996) Cell 85:319–329). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

A "knock-in" of a target gene means an alteration in a host cell genome that results in altered expression or function of the native SARG-1. Increased (including ectopic) or decreased expression may be achieved by introduction of an additional copy of the target gene, or by operatively inserting a regulatory sequence that provides for enhanced expression of an endogenous copy of the target gene. These changes may be constitutive or conditional, i.e. dependent on the presence of an activator or re-presser.

The exogenous gene is usually either from a different species than the animal host, or is otherwise altered in its coding or non-coding sequence. The introduced gene may be a wild-type gene, naturally occurring polymorphism or mutation, or a genetically manipulated sequence, for example having deletions, substitutions or insertions in the coding or non-coding regions. The introduced sequence may encode wild-type human or animal SARG-1 protein or a mutation thereof, or may utilize the SARG-1 promoter operably linked to a reporter gene. Where the introduced gene is a coding sequence, it is usually operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g. transcriptional activator proteins, are bound to the regulatory sequence s).

Specific constructs of interest, include, but are not limited to anti-sense SARG-1, which will block native SARG-1 expression, expression of dominant negative SARG-1 mutations, and over-expression of a SARG-1. A detectable marker, such as lac Z may be introduced into the locus, where upregulation of expression will result in an easily detected change in phenotype. Constructs utilizing the SARG-1 promoter region, in combination with a reporter gene or with the coding region are also of interest.

A series of small deletions and/or substitutions may be made in the SARG-1 to determine the role of different exons in DNA binding, transcriptional regulation, etc. By providing expression of SARG-1 protein in cells in which it is otherwise not normally produced, one can induce changes in cell behavior.

DNA constructs for homologous recombination will comprise at least a portion of the SARG-1 with the desired genetic modification, and will include regions of homology to the target locus. DNA constructs for random integration need not include regions of homology to mediate recombination. Conveniently, markers for positive-and negative selection are included. Methods for generating cells having targeted gene modifications through homologous recombination are known in the art. For various techniques for transfecting mammalian cells, see Keown et al. (1990) Methods in Enzymology 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopreg-nant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture.

Binding partners of human SARG-1 include protein-O-mannosyltrans-ferase 1 (POMT1), microtubule-associated protein 1 A (MAP1A), ATpase, Na+/K+ transporting beta 1 polypeptide (ATP1B1), SWI/SNF complex 60 KDa subunit (BAF60c) alpha-Actinin 2, exon 16, rab GDP dissociation inhibitor 1 (GDI1) and proteasome 26 S subunit, ATPase 3 (PSMC3).

Is is a further aspect of the present invention to use SARG-1 binding proteins for modulating activity of SARG-1 proteins (including mutants) and vice versa. Moreover, SARG-1 (wild type) or SARG-1 binding proteins may be used for treating MS or cancer, preferably myeloproliferative disorders, polycythaemia, myelodys-plasia and myeloid leukaemia, especially acute myeloid leukaemia, by administering an effective amount of SARG-1 or SARG-1 binding protein (or a complex thereof) to an MS or cancer patient. Instead of wt-SARG-1 protein, also fragments of SARG-1 may be used which are suitable for advantageous treatment of such patient (e.g. fragments binding to the SARG-1 binding proteins). Minimum requirements for such fragments are easily found by the skilled man in the art especially using the mouse models described herein.

BRIEF DESCRIPTION OF THE DRAWINGS

The method is further described by the examples and drawing figures, without being restricted thereto.

FIG. 1 shows reverse northern blot demonstrating induction of the rat SARG-1 gene during apoptosis. Plasmid DNA was spotted onto nylon membranes and hybridised with radiolabelled cDNA isolated from apoptotic stem cells. Plasmids containing the 5' region of SARG-1 (arrowed) hybridise with cDNA only present in apoptotic cells. Control cDNA from self-renewing cells showed only background levels (data not shown).

FIG. 2 shows rat multiple tissue northern blot. The 342 bp SARG-1 fragment was radiolabelled and hybridised with RNA isolated from different rat tissues. A species of approximately 1.4 Kb is observed with an ubiquitous tissue distribution and highest expression in brain and heart.

FIG. 3 shows mouse embryonic tissue northern blot. The 342 bp SARG-1 fragment was radiolabelled and hybridised with RNA isolated from various stages of embryonic development. Clear regulation of a 1.4 Kb species is seen with highest levels after 7 days and re-expression of the gene product on day 17.

FIG. 4 shows full length rat mouse and human SARG-1 cDNA sequences.

FIG. 5 shows comparisons between full length rat mouse and human SARG-1 cDNA sequences.

FIG. 6 shows full length rat, mouse and human SARG-1 coding sequences with corresponding predicted amino acid sequence.

FIG. 7 shows comparison between the tat, mouse and human SARG-1 DNA coding sequences.

FIG. 8 shows comparison between the rat, mouse and human SARG-1 amino acid coding sequences.

FIG. 9 shows immunohistochemical analysis of mouse tissue with anti-SARG-1 peptide antibodies. A brown reaction product indicates SARG-1 expression. A: Mouse cerebral cortex (magnification ×40), B: Cerebellum (×40), C: Spinal chord (×40), D: Peripheral nerve (×60), E: Heart (×40) and F: Lung tissue (×40).

FIG. 10 shows SARG-1 protein detected by western blotting of cellular extracts from MelJUSO melanoma cells transfected with pMH-SARG-1-HA. Anti-HA monoclonal antibody 3F10 detected a single species which migrates at 28 kD.

FIG. 11 shows immunohistochemical analysis of human SARG-1 protein in MELjuso cells transfected with pMH-SARG-1-HA detected by the anti-HA monoclonal antibody 3F10 demonstrating cytoplasmatic localisation of the protein.

FIG. 12 shows viability of PC12 cultures transfected with empty vector or pIRES2-EGFP-SARG-1 treated with 100 nM staurosporine.

FIG. 13 shows flow cytometrical analysis of PC12 cells transfected with empty vector or pIRES2-EGPP-SARG-1 treated with 100 nM staurosporine for 24 h. A sub $G_0/G_1$ peak characteristic for the induction of apoptosis is seen only in SARG-1 over-expressing cells.

FIG. 14 shows PC12 cells that overexpress SARG-1 protein (■) undergo accelerated NGF-mediated terminal differentiation when compared to cells transfected with empty vector (♦).

FIG. 15 shows genetic alteration in familial multiple sclerosis. A T→C point mutation at nucleotide 67 resulting in the substitution of leucine for phenylanaline amino acid 23.

FIG. 16 shows genetic alteration in familial multiple sclerosis. A C→T point mutation at nucleotide 359 resulting in the substitution of phenylanaline for serine at amino acid 120.

FIG. 17 shows genetic alteration in familial multiple sclerosis. An A→G point mutation at nucleotide 89 resulting in the substitution of glycine for glutamic acid at amino acid 30.

FIG. 18 shows genetic alteration in familial multiple sclerosis. Deletion of a codon between amino acids 116 and 121 resulting in the loss of a serine residue.

FIG. 19 shows the SARG-1 intron/exon structure.

EXAMPLES

Figure 1:
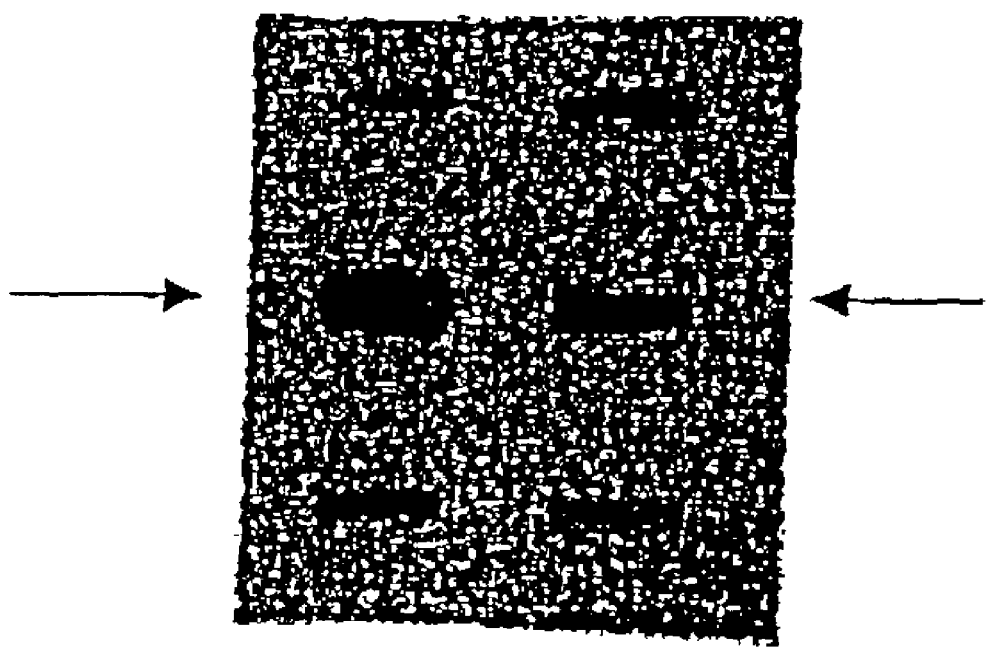

Identification of a Novel SCF-Apoptosis-Response-Gene (SARG-1) Induced During Stem Cell Apoptosis Withdrawal of growth factor from SCF dependent myelomonocytic progenitors results in rapid induction of cell cycle-independent apoptosis. Although over 95% of SCF-deprived cultures exclude vital dyes 12 hours after growth factor withdrawal, no proliferative response is seen on restimulation with SCF after this time point. A differential display screen was conducted to examine immediate-early (four hour) RA expression differences during the processes of myelomonocytic stem cell self-renewal and apoptosis induced by growth factor withdrawal. Amplification of approximately ⅓ of all cellular mRNA species by differential display PCR (Liang and Pardee 1992, 1995; Liang et al, 1993) with defined primer (Bauer et al, 1993) sets (Display systems) identified one fragment induced during apoptosis not present in self-renewing precursors. Following gel excision of this band and TA cloning into the pCR°II vector (Invitrogen) of reamplificants, specific expression induction was confirmed in a reverse northern procedure with representative dot blotted plasmid preparations hybridised with radiolabelled cDNA isolated prepared from independent cultures (FIG. 1). All positively identified differentially regulated clones were sequenced and found to contain an identical 342 base pair insert (excluding the downstream and upstream differential display primer pairs).

Figure 2:
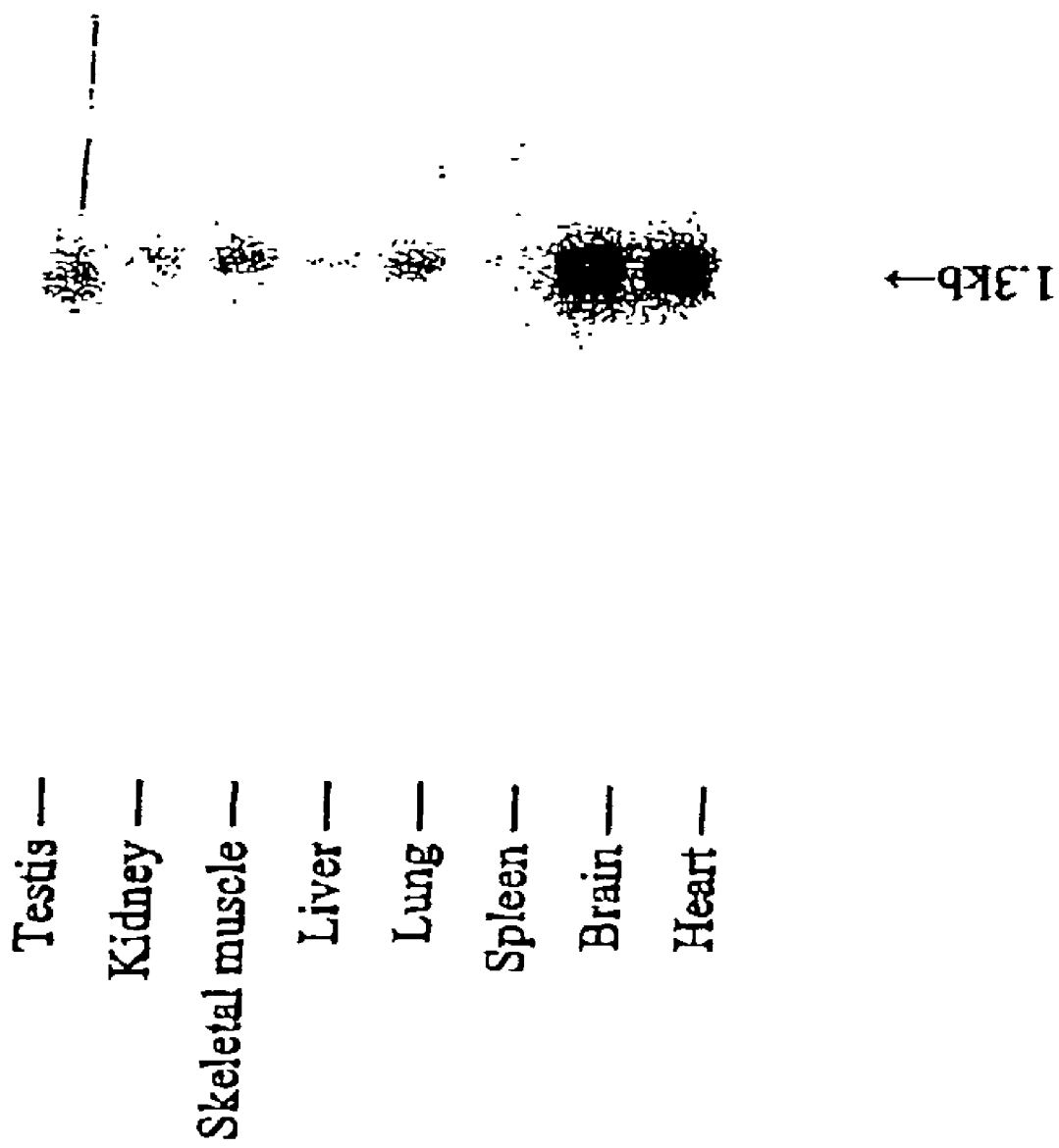
Figure 3:
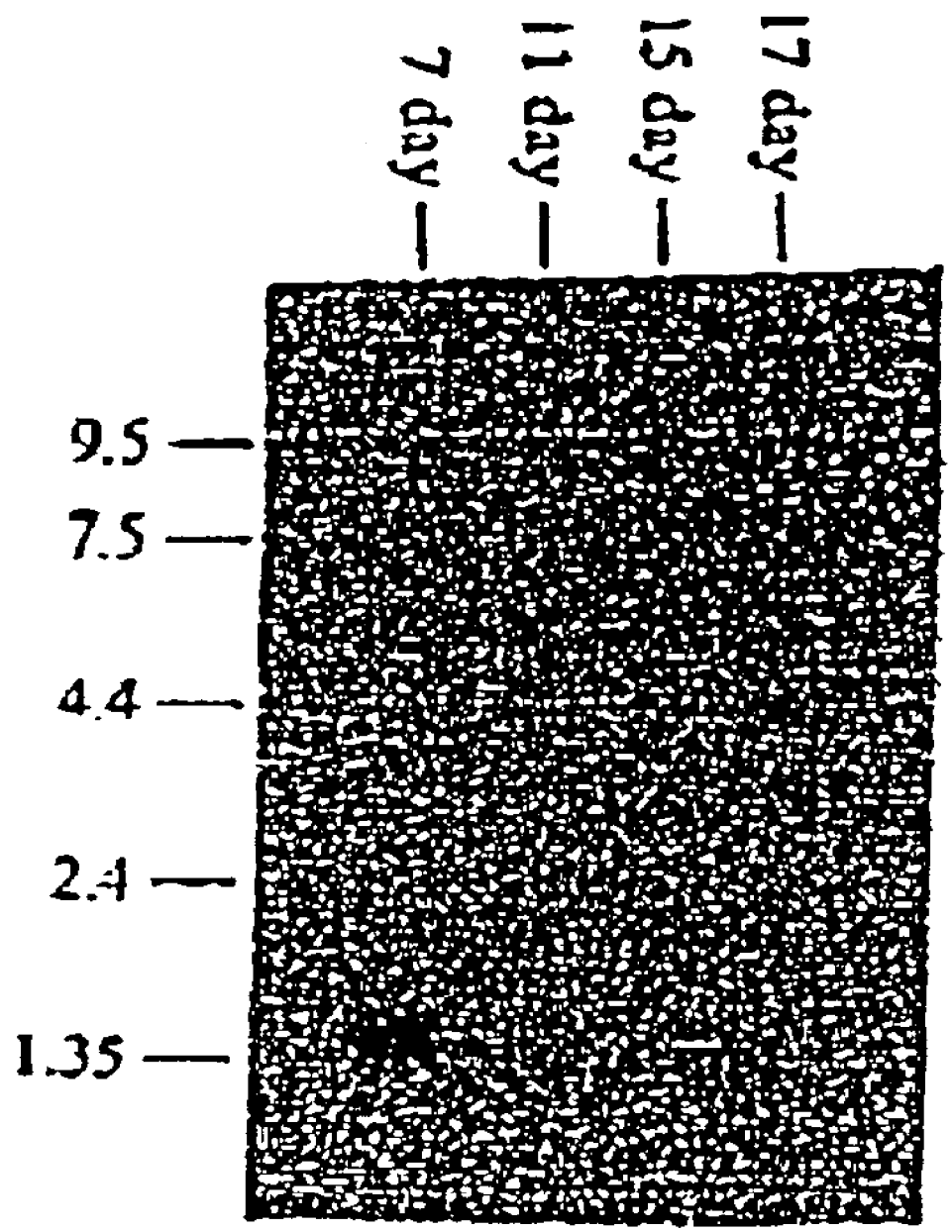

Molecular Weight of SARG-1 cDNa and Tissue Expression. Regulation During Embryonic Development Radioactive labelling of the 342 bp fragment discovered above and probing of multiple tissue northern blots (Clontech) showed an approximately 1300 bp length for the mature mRNA in rat, mouse and human tissues. An ubiquitous low expression was seen with highest expression levels in brain and heart (FIG. 2). Northern blots of immobilised mRNA isolated from different stages of murine embryonic development probed with the radioactively labelled 342 bp fragment demonstrated regulation of SARG-1 mRNA during development with highest levels after 7 days and re-expression of the gene product on day 17 (FIG. 3).

Cloning of Full Length Rat, Murine and Human SARG-1.

Figure 5:
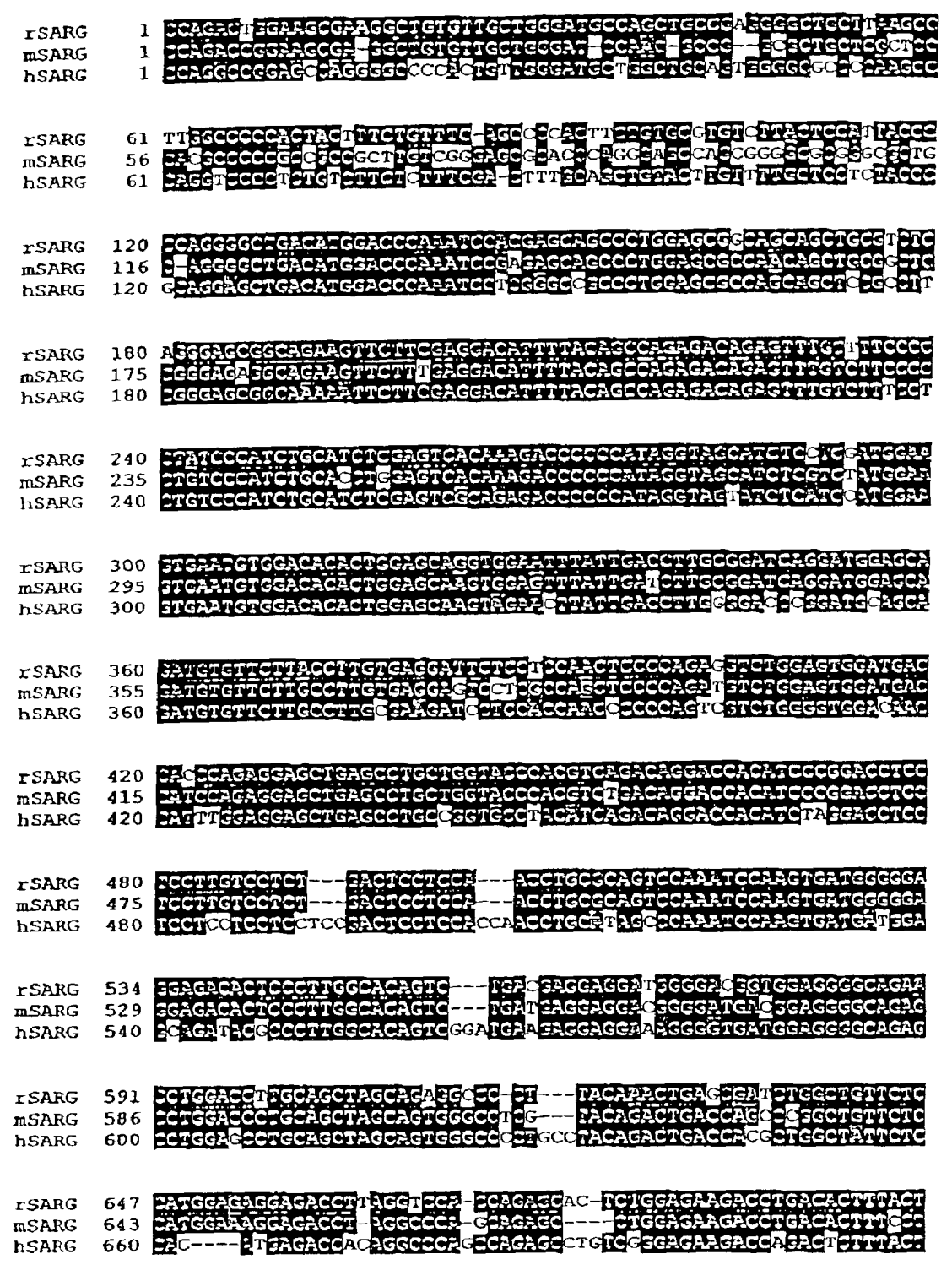
Figure 5:
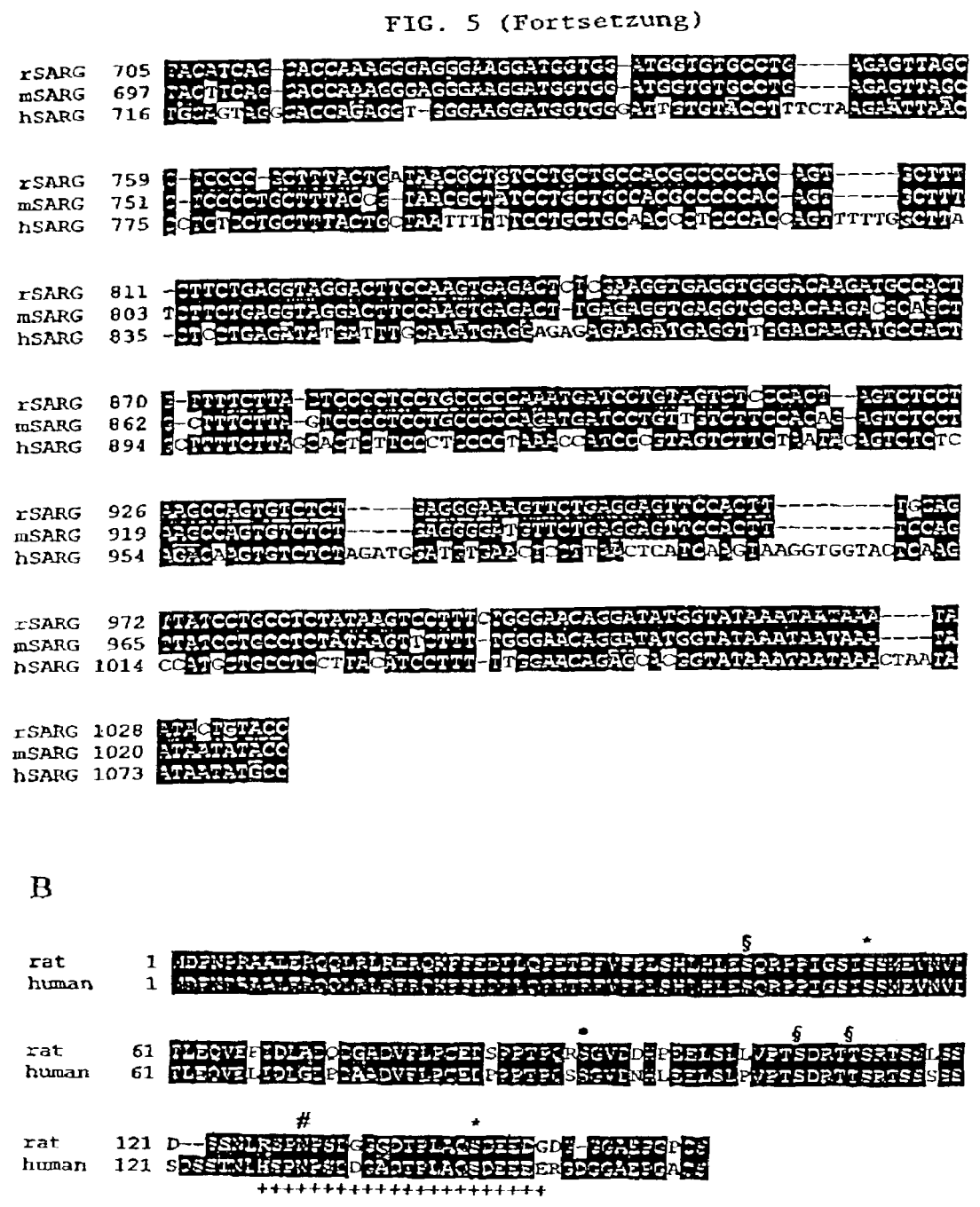

Additional SARG-1 sequence information was obtained by a 5' rapid amplification of cDNA ends polymerase chain reaction (RACE) procedure from adapter ligated rat brain Marathon-ready cDNA (Clontech,). A primer was constructed at the 3' proximal end of the 342 bp sequence and the PCR product cloned into the pCR® TA cloning vector (Invitrogen) and sequenced. The full length SARG-1 1062 bp gene transcript was sequenced and has a 479 bp open reading frame which encodes a 158 amino acid protein. Murine SARG-1 was isolated by screening a bacterial artificial chromosome bank derived from mouse strain 129SvJ with the full length rat SARG-1 cDNA. Homologous clones were isolated and a Xho I fragment seguenced. Mature murine SARG-1 RNA was then identified by PCR from mouse brain cDNA. Human SARG-1 was isolated from a phage bank of brain cDNA by homology to the full length rat sequence and sequenced. The full-human SARG-1 locus was amplified by PCR with primers spanning the SARG-1 cDNA from chromosomal DNA isolated from the peripheral blood mononuclear cells of healthy volunteers. The full length sequences of rat, mouse and human SARG-1 are shown in FIGS. 4, 5 and 6.

The Homologies Between Rat, Mouse and Human Sequences

Rat and mouse SARG-1 are 93% at the nucleic acid and 96% homologous at the predicted protein levels, respectively. Human SARG-1 displays 83% and 84% homologies to mouse and rat SARG-1 at the nucleic acid level and 84% and 86% homologies at the predicted protein levels, respectively (FIGS. 7 and 8), and is localised to the long arms of chromosome 20 (at 20q13.12 (Deloukas et al., 2001)), deletion of which are a common occurance in a wide range of myeloproliferative disorders (Wattel et al, 1993 and Bench et al., 2000). Sequences contain a potential PEST region (Rechsteiner et al. 1996) (+), a single conserved potential N-glycosylation site (#) and three conservers PKC (§) and casein kinase II (*) phosphorylation sites (see FIG. 5B).

Analysis of SARG-1 Distribution with Anti-SARG-1 Antibodies

SARG-1 antibodies were prepared by immunising chickens with a peptides (MDPNPAALERQQLR and DEEEERGDGQAEPGA) corresponding to the first 15 amino acids and to the c-terminal part of mouse, rat and human SARG-1 coupled to keyhole limpet hemocyanin. IgY was prepared from egg yolks and specific antibody prepared by affinity chromatography with column-immobilised peptide.

Figure 9A:
Figure 9B:
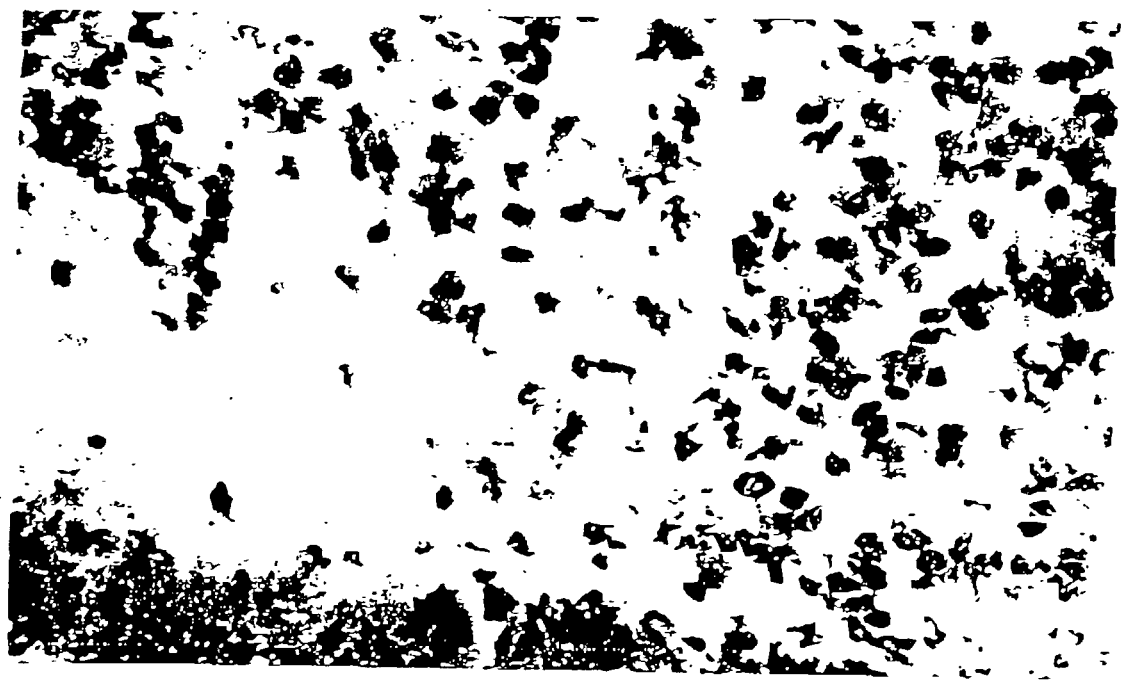
Figure 9C:
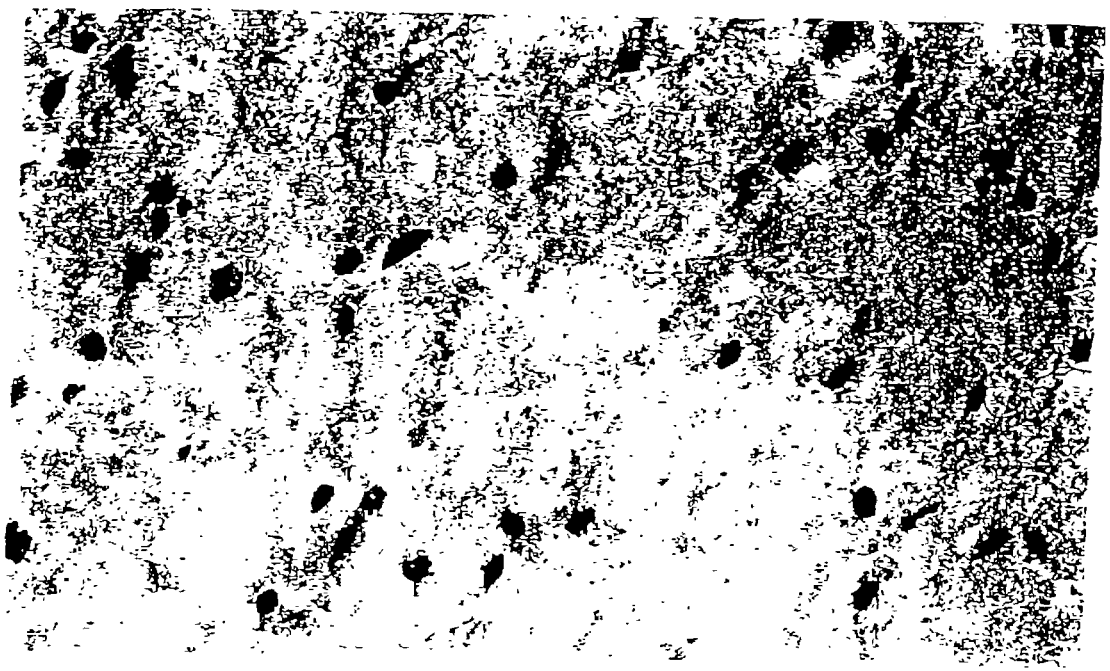
Figure 9D:
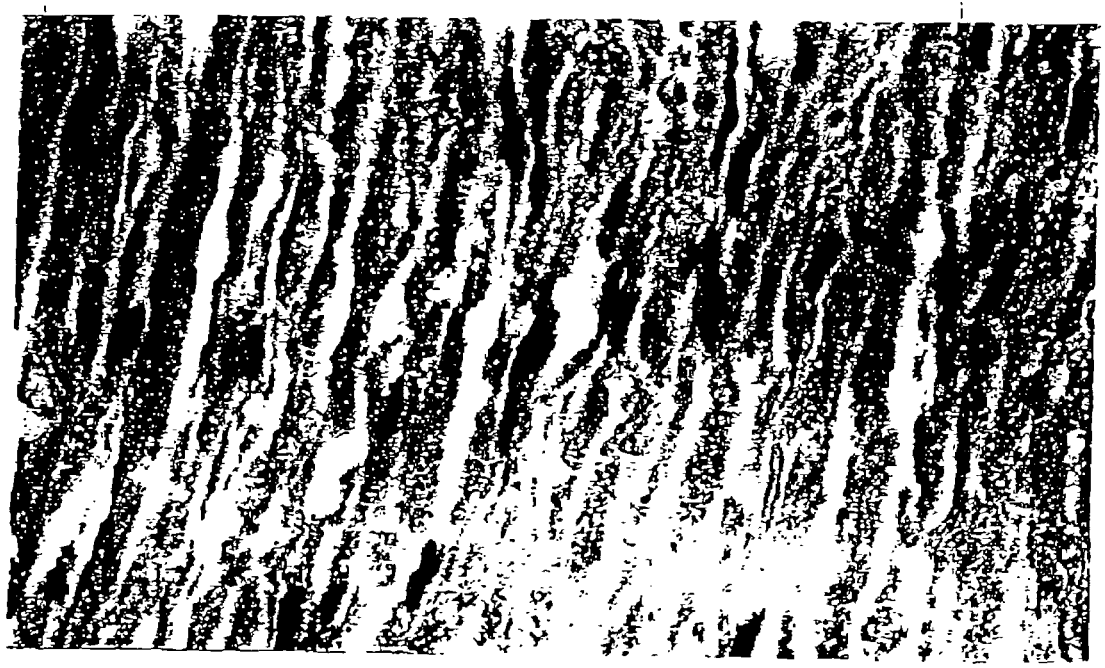
Figure 9E:
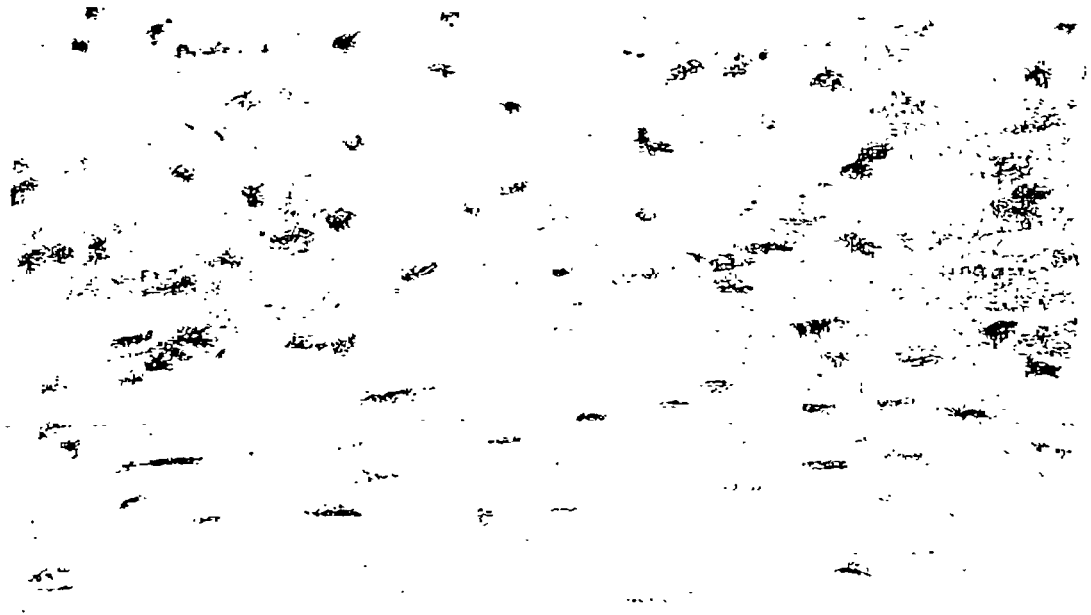
Figure 9F:
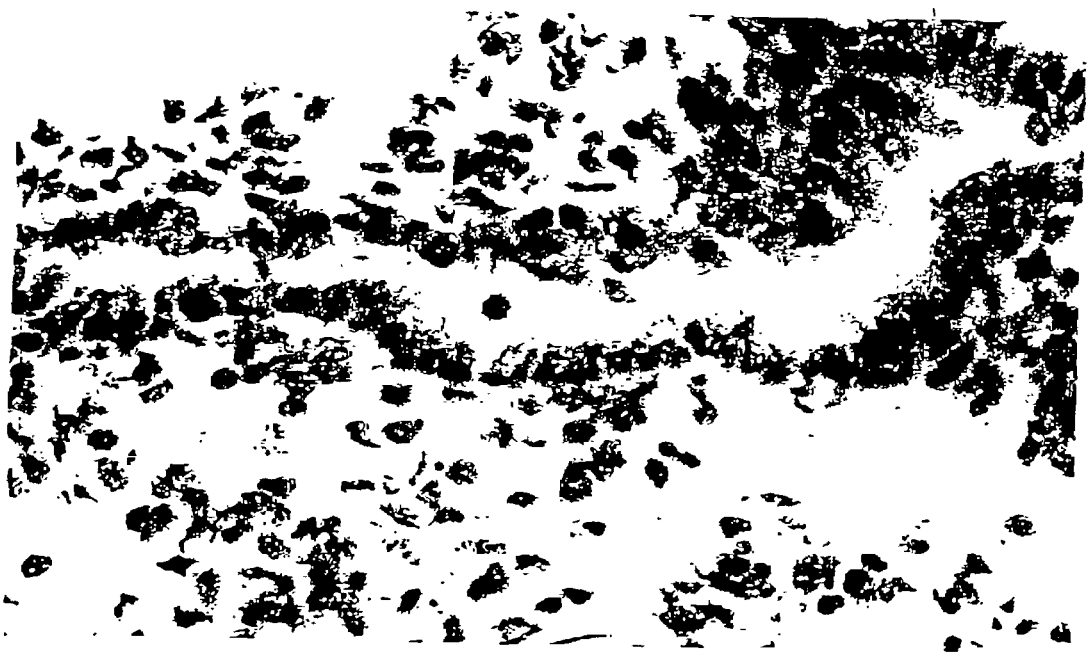

In immunohistochemical analysis of 5 mm acetone-fixed sections of mouse tissue, specific anti-SARG-1 IgY antibodies visualised with anti-IgY peroxidase conjugated second step antibodies, detected wide expression of the SARG-1 protein in nervous tissue. SARG-1 staining is seen throughout the cerebral cortex (FIG. 9A) and within the granular, Purkinje and molecular cell layers of the cerebellum (FIG. 9B). In the spinal chord, SARG-1 is expressed in both the gray matter neurophil containing nerve cell bodies, dendrites, glial cells and blood vessels and the white matter consisting largely of myelinated nerve tracts (FIG. 9C). SARG-1 expression is also colocalised to occasional peripheral nerve processes (FIG. 9D). SARG-1 is also ubiquitously expressed in cardiac muscle, (FIG. 9E), lung ciliated epithelia (FIG. 9F) and epithelial cells of the ileum and colon (data not shown). Staining of mouse embryonic tissue demonstrated strong staining of neural tissue, brain, heart, placenta, uterus, the organ of corti, the dermis (stratum granulosum) and lining of the gut (data not shown).

Generation of SARG1 Over-dressing Cells

The MelJUSO melanoma cell line was maintained in Dulbecco's modified eagles medium (DMEM) supplemented with 10% fetal calf serum and an antibiotic-antimycotic mix containing 100 units/ml penicillin 100 µg/ml streptomycin, and 0.25 µg/ml amphotericin B (all from GibcoBRL) in a fully humidified air atmosphere containing 5% $CO_2$ at 37° C. The human SARG-1 coding sequence (hSARG-$1_{485}$) was cloned into the pMH expression vector (Roche) by standard molecular biology procedures (Sanbrook et al, 1989) under the control of a CMV promoter in frame with a c-terminal hemaglutinin (HA) peptide sequence. Semi-confluent cultures in 6 well plates were transfected with this vector (pMH-SARG-1-HA) or empty vector in the presence of Fugene (Roche) and clones isolated which displayed resistance to neomycin.

To examine the expression and function of SARG-1 in a neural cell culture system, standard molecular biology techniques (Sanbrook et al, 1989) were used to clone the rat SARG-1 coding sequence (rSARG-$1_{479}$) into the pIRESII-EGFP eukaryotic expression vector (Clontech) under the control of a CMV promoter which bicistroni-cally translates through an internal IRES sequence both SARG-$1_{477}$ and enhanced green fluorescent protein. The rat pheochromocytoma PC12 cell line was maintained in DMEM supplemented with 8% horse serum, 8% fetal calf serum and an antibiotic-antimycotic mix containing 100 units/ml penicillin, 100 µg/ml streptomycin, and 0.25 µg/ml amphotericin B (all from GibcoBRL) in a fully humidified air atmosphere containing 5% $CO_2$ at 37° C. Semi-confluent cultures in 6-well plates were transfected with pIRES2-EGFP-SARG-1 or empty vector for 18 h in the presence of the uptake enhancing cationic lipid mix pFx1 (Invitrogen) at a 6:1 lipid to DNA ratio in serum-free opti-MEN (Gibco). Stable transfectant colonies were picked from separate wells after selection in 800 mg/ml geneticin (Gibco) and clones with similar EGFP fluorescence expanded from independent transfections.

Post Translational Modification of Mature Rat and Human Proteins

Figure 10:
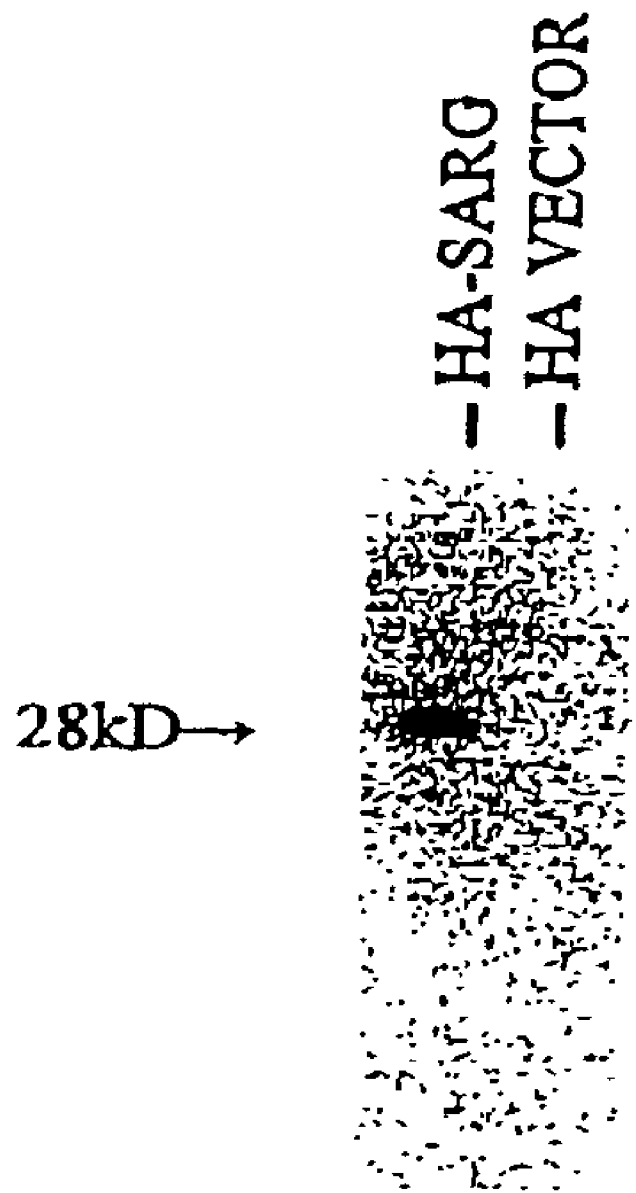

The molecular weights of rat, mouse and human SARG-1 protein predicted from the amino acid sequences are 17186.52, 17193.52 and 17492.76, respectively. IgY antibodies against SARG-1 detect a 28 kD species in western blotting expressed at low levels in native PC12 cells. Upon transfection of pIRES2-EGFP-SARG-1 into these cells, expression levels of this species increase. The molecular weight of human SARG-1 protein was determined by western blotting of cellular extracts from MelJUSO melanoma cells transfected with pMH-SARG-1-HA. Anti-HA monoclonal antibody 3F10 (Roche) detected a single species which migrates at 28 kD (FIG. 10).

Subcellular Localisation of Transfected SARG-1 Protein

Figure 11:
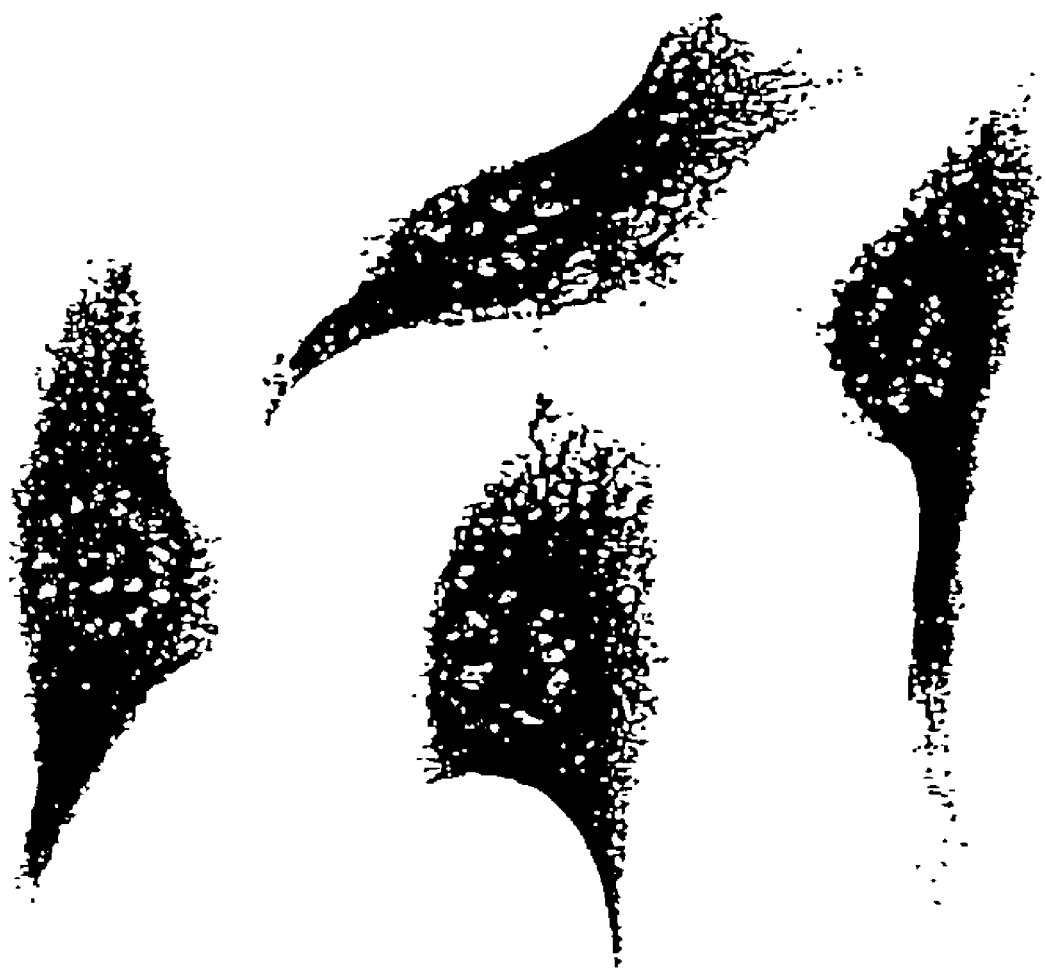

Immunohistochemical staining of SARG-1 transfected PC12 cells demonstrated an exclusive cytoplasmatic localisation for the SARG-1 gene product. Immunohistochemical analysis with anti-HA monoclonal antibody 3F10 also demonstrated an exclusive cytoplasmatic localisation for the SARG-1 protein (FIG. 11) primarily colocalising with expression of binding protein (bip) used as marker for the endoplasmatic reticulum. Co-localisation of HA-SARG-1 with the golgi-specific antigen coat protein (b-cop) is minimal. In contrast, SARG-1 expression partly overlaps with expression of the lysosomal specific protein LAMP-2.

Role of SARG-1 in Apoptosis and Differentiation of Neural Cell Cultures

Figure 12:
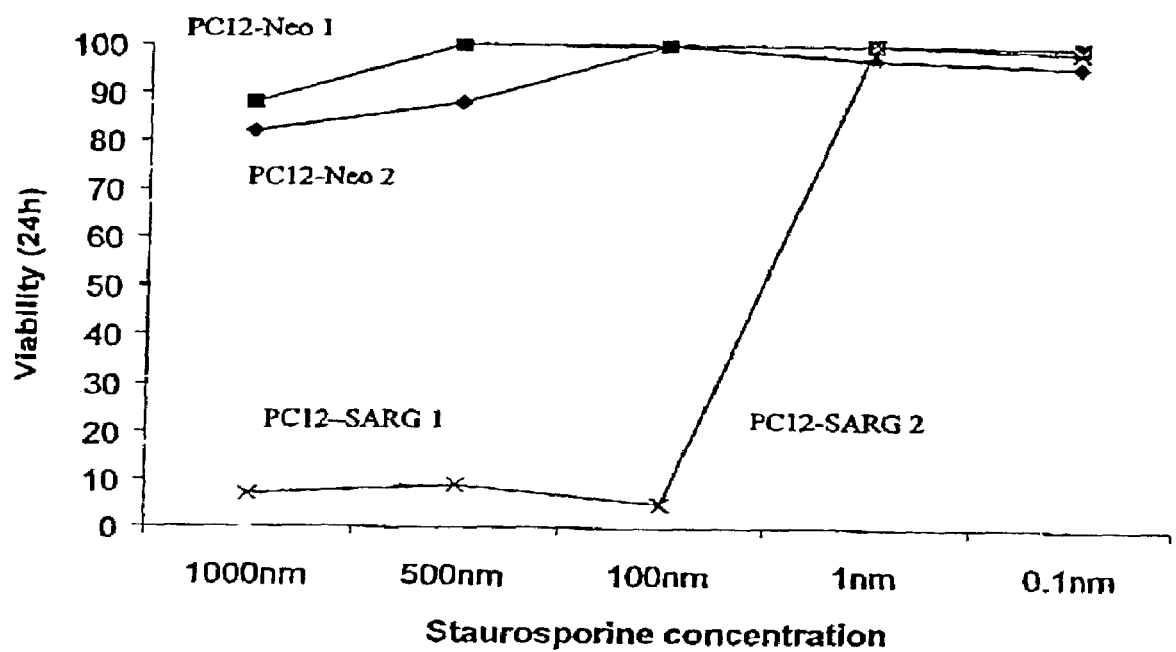
Figure 13:
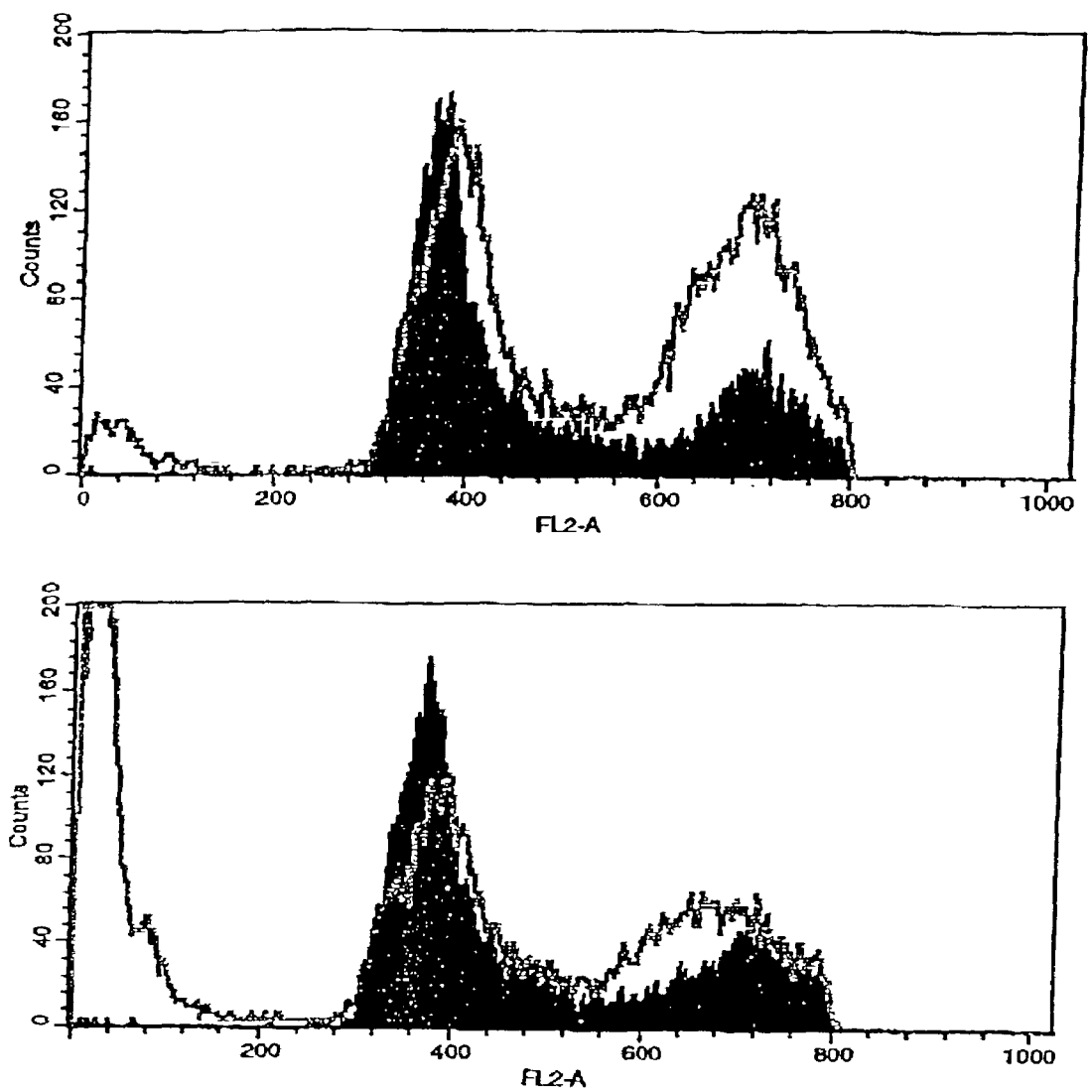
Figure 14:
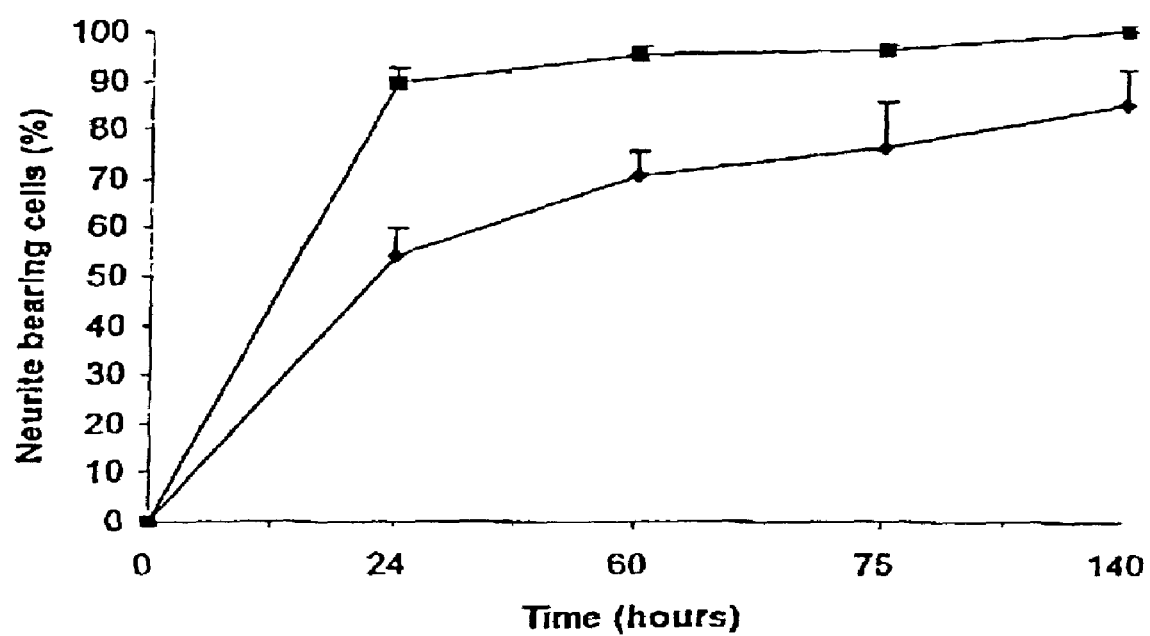

Treatment of PC12 cells with the protein kinase inhibitor staurosporine induces neurite outgrowth at concentrations of 100 nM (Hashimoto and Hagino, 1989) and apoptosis at concentrations above 1 mM (Fu et al, 1999). SARG-1 over-expressing PC12 cells undergo a rapid loss in viability on treatment with 100 nM staurosporine (Calbiochem) in comparison to vector control cultures (FIG. 12) which undergo neurite outgrowth. Cell death in SARG-1 over-expressing PC12 cultures is accompanied by cell shrinkage, development of a morphology characteristic of programmed cell death and loss of DNA from ethanol fixed cells in flow cytometrical cell cycle analyses (FIG. 13) characteristic of the apoptotic process (Fraker et al, 1995). No similar effects are seen with the staurosporine analogue X252a (Alexis), the phosphatidylinositol 3-kinase inhibitors LY-294002 (Alexis) or Wortmannin (Calbiochem), the MAP kinase kinase inhibitor PD 98059 (Alexis) or the protein kinase C inhibitor Bisindolylmaleimide I (Alexis). Over-expression of SARG-1 also enhances terminal differentiation of PC12 cells induced by nerve growth factor (FIG. 14).

Isolation of SARG-1 Binding Proteins

Yeast two hybrid screening are performable with the commercially available Matchmaker system from Clontech. The bait plasmid is constructed by cloning the full length hSARG-1 coding sequence into the pGBKT7 shuttle vector (Clontech) by PCR using the BamH1 and, EcoR1 restriction sites using standard methods (shuttle vector pGBKT7: The coding region of hSARG-1 is cloned as a c-terminal fusion to amino acids 1-147 of the GAL4 DNA binding domain (DNA-BD) containing a c-myc tag under the control of the yeast ADH1 promoter (P) by PCR amplification using the EcoR1 and BamH1 restriction sites and selected in yeast using the TRP1 nutritional marker). This construct is then used to lithium acetate transform the MATa yeast strain AH109 which is auxotrophic for adenine (Ade), histidine (His) leucine (Leu) and tryptophan (Trp) and selected for pGBKT7 by growth on synthetic dropout (SD)-Trp medium, A human brain matchmaker library (Clontech) directionally constructed in pACT2 pretransformed in the MATα Y187 (Ade$^-$, His$^-$ Leu$^-$ and Trp$^-$) yeast strain is purchased and at least $3 \times 10^6$ clones mated with AH109 transformed hSARG-1-1 (shuttle vector pACT2: Human brain library inserts are directionally cloned in frame as c-terminal fusions to amino acids 768-881 of the GAL4 activation domain, the SV40 T-antigen nuclear localization sequence and a HA epitope tag under the control of the yeast ADH1 promoter (P) and selected in yeast using the LEU2 nutritional marker). Zygotes are isolated by Leu$^-$ and Trp$^-$ selection and protein interactions simultaneously by reporter gene activation of HIS3, ADE2, and MEL1 on -His, -Ade plates containing X-α-Gal (5-Bromo-4-chloro-3-indolyl-a-D-galactopyranoside), respectively. Positive colonies are restreaked and additionally tested for lacZ reporter activation with β-galactosidase. The inserts from positive colonies are amplified by PCR, repeats identified by restriction digestion and positive interactors identified by short run sequencing from the adapter end of the insert. The identity of potential interactors are ascertained by FASTA and BLAST searches against non-redundant and expressed sequence tag data bases at the national centre for biotechnology information (www.ncbi.nlm.nih.gov/BLAST/) and European bioinformatics institute (www.ebi.ac.uk/fasta33/) interfaces, respectively, to identify characterized proteins cloned in frame with the GAL4 activation domain. Single pACT2 plasmids are then recovered by transformation of E. coli under ampicillin selection and positive interactions retested by cotransformation of AH109 with pGBKT7-SARG-1 and pACT2 containing the library insert selected by blue colony growth on -Ade, -His, -Leu, -Trp, X-α-gal plates. Bait and library genes are cloned into appropriate c-myc and HA epitope tagged eukaryotic expression vectors and interactions further confirmed by Western blotting of coimmuno-precip-tated proteins either translated in vitro or from transiently cotransfected HEK 293 cells. The latter also allows colocaliza-tion experiments by confocal microscopical analysis following cloning and isolation of full length coding sequences. The cellular co-expression of interaction partners with SARG-1 is examined by either staining of sequential embryological slides generated with antibodies where available or by in situ hybridization of identified sequences. The identification of known binding partners enables the development of antisense or RNAi strategies to specifically reduce target expression or allows the use of specific functional inhibitors to further characterise the phenotypic changes seen in PC-12 apoptosis and differentiation. Binding partner identification also identifies the biochemical pathways which are influenced by SARG-1 expression which may also be specifically inhibited. Knockout models for identified binding partners may be crossed with the SARG-1 deficient mouse.

Pitfall Analysis

A relevant tissue is analysed where SARG-1 is highly expressed and plays a role in differentiation and apoptosis in a cell line model. Human gene banks are analysed to enable rapid identification of known RNA sequences. The SARG-1 sequence contains no cytoplasmic localization signals which could reduce transcriptional activation. Transfection of SARG-1 is not directly toxic to PC-12 or MelJuso cells and is therefore unlikely to be toxic in yeast. The matchmaker system uses multiple reporter genes with different promoter constructs to eliminate artefacts and has been used to isolate a number of binding partners (Corset et al, 2000; Galiegue et al, 1999; Ono et al, 2000; White et al, 2000). A eukaryotic cell line (HEK293) which allows efficient transient co-transfection of vector constructs is used to allow rapid screening of putative binding partners.

In a yeast two-hybrid analysis using the human SARG-1 protein as a bait to screen a human brain cDNA ebank the following binding partners were isolated:

1; Homo sapiens protein-O-mannosyltransferase 1 (POMT1), (LC2)mRNA: (gi: 12734916)
2: Homo sapiens microtubule-associated protein 1A (MAP1A), mRNA (XM_012387)
3: Homo sapiens ATPase, Na+/K+ transporting, beta 1 polypeptide (ATP1B1, mRNA (gi: 4502276)
4: Human SWI/SNF complex 60 KDa subunit (BAF60c) mRNA (gi: 1549246)
5: Homo sapiens ACTN2 gene for alpha-Actinin 2, exon 16 (gi: 6448557)
6: Homo sapiens rab GDP dissociation inhibitor 1 (GDI1), mRNA (gi: 4503970)
7: Homo sapiens proteasome (prosome, macropain) 26S subunit, AT-Pase, 3(PSMC3), mRNA (gi: 4506210)

Of these binding proteins, especially the ATPase beta 1 polypeptide is of specific interest for use as a pharmaceutical target with respect to the binding to SARG-1.

Generation of a Conditional SARG-1 Knockout Mouse

Effective homologous recombination between vector construct and chromosomal target sequences is normally achieved by a species specific region of homology of 7 kb with at least 2 kb of homologous material adjacent to the drug resistance cassette (Johnson et al., 1995). The murine SARG-1 locus has been fully amplified by PCR (2420 bp) and sequencing demonstrated the presence of 3 introns.

For construction of the replacement vector, approximately 2.5 kb of additional non-coding chromosomal sequence information flanking the SARG-1 locus are obtained in the 129SvJ mouse. To this end, a radiolabelled SARG-1 cDNA sequence or a PCR product of the entire mSARG-1 locus is used to screen a 129SvJ mouse bacterial artificial chromosome (BAC) library (Incyte genomics) with an average insert size of 120 kb or a 129SvJ mouse genomic library constructed in Lambda FIX® II phage (Stratagene) with insert sizes of 9 to 23 kb, by standard methods. Following clone or phage isolation, genomic sequences flanking the coding region (approximately 2.5 kb) is characterized by either direct sequencing of isolated clones with primers internal to the SARG-1 coding region, sequencing of cloned restriction fragments bearing SARG-1 sequences or by inverse PCR. The sequence information obtained is used to design PCR primers to insert 129SvJ mSARG-1 genomic sequences into the conditional/hypomorphic pDELBOY-3X targeting vector (Rossi et al, 2001). This vector incorporates features that overcomes problems potentially associated with gene deletion. Artifactual phenotypes are generated in knockout mice due to the transcriptional activity of the neomycin cassette which can lead to disrupted regulation and splicing of the target locus and neighbouring genes (Pham et al, 1996; Olson et al, 1996). The neomycin cassette in the pDELBOY-3X vector is flanked by flip recombinase (frt) sites which permit efficient excision of the selection cassette in vitro and in vivo. Transient transfection of cells stably transfected with pDELBOY-3X with a vector expressing Flp recombinase leads to excision of the neomycin cassette.

Recently developed tools such as Flp recombinase-GFP fusion protein vectors, for example, allow enrichment of Flp-mediated recombination events in vitro by fluoresence activated cell sorting (Sabath et al., 2000). Conversely, crossing mice with the 129SvJ FLPer deleter mouse ubiquitously expresssing enhanced FLP allows excision of the neomycin cassette in vivo. In addition, cloning of SARG-1 coding sequences between the loxP sites in the pDELBOY3X vector permits generation of a null allele either in vitro by transfection with cre recombinase expressing plasmids or in vivo by crossing mice generated with animals expressing cre recombinase in a tissue specific or. This strategy eliminates problems associated with heterozygote embryonic lethality and allows the precise tissue specific analysis of protein function. Knockout mice are generated by standard procedures (Papaioannou and Johnson, 2000; Gu et al, 1993). Briefly, embryonic stem cells (ES) are transfected by electroporation with linearized pDELBOY-3X-SARG-1 and homologous recombination events selected by neomycin/gancyclovir treatment and clones screened by PCR or southern blotting with a radiolabelled probe external to the targeting sequences. Blastocytes are isolated from 3.5 day pregnant mice, injected with ES clones and reimplanted in pseudopregnant mice. Following coat colour selection of chimeras, founder animals are mated with normal 129SvJ mice to produce a breeding line. Homozygotes are subsequently be obtained by inter-breeding. The phenotype of mice are screened by standard procedures. Analysis of histological sections prepared from embryonic and adult tissue, magnetic resonance imaging analysis combined with cell death assays such as TdT-mediated dUTP-X nick end labelling (TUNEL) provides direct evidence of the role of SARG-1 in differentiation and apoptosis, respectively, during development. Cellular analysis includes hematopoietic stem cell characterisation (colony forming assays, flow cytometrical analysis for cluster of differentiation antigens) and apoptotic response measurements in neural culture systems.

Pitfall Analysis

As described above, the pDELBOY-3X vector eliminates artefacts produced by transcription from the neomycin cassette and overcomes the problems of heterozygote embryonic lethality. Screening is also aided by the availability of animals which have a single mutation in the c-kit gene. Identification of SARG-1 binding partners for which knock-out mice exist allows breeding with SARG-1 deficient mice to further clarify phenotype.

Cellular Localization

Balb/c mice are mated and embryos isolated at 7, 11 (Theiler's stages 10-19), 14 and 17 days and snap frozen in liquid Nitrogen. 5 µm transverse and sagittal consecutive sections are made on a cryostat and frozen until required. SARG-1 expression is analysed by standard immunohistochemical analysis on sections with anti-SARG-1 IgY which detects acetone-fixed mSARG-1. Expression patterns are identified by reference to standard embryological texts (Kaufman, 1992) and the mouse atlas and gene expression database project (http://genex.hgu.mrc.ac.uk/). Expression patterns in 17 days embryos are additionally correlated with those seen in adult murine tissue. Following identification of SARG-1 binding partners, co-expression studies are performed either by immunohistochemistry if antibodies are available or in situ hybridisation.

Subcellular Localization and Biochemical Characterization of Epitope Tagged SARG-1

The cytoplasmic, vesicular subcellular localization of SARG-1 is determined by double staining of HEK293, MelJuso or PC-12 cells stably transfected with epitope-tagged SARG-1. The HA tag is stained with rat monoclonal anti HA mAb and visualised with a biotinylated monoclonal anti-isotype mAb followed by fluorochrome conjugated streptavivin (FITC, S, phycoerythrin or cy5) Organelle localized antigens are detected with antibodies to Bip/GRP78 (endoplasmic reticulum), β-cop (Golgi complex), Lamp-1 (lysosomes) and Ab-2 (mitochondria) either conjugated directly or by the use of second step antibodies and analysed on a Zeiss laser scan microscope. Cloned and native SARG-1 (predicted mass 17 Kd) migrates at 28 Kd in SDS-PAGE. Glycosylation of HA-tagged SARG-1 is initially investigated by immunoprecipitation on an anti-HA matrix and detection of glycosylated residues by periodate oxidation, incorporation of biotin hydrazide and detection with streptavidin conjugated alkaline phosphatase on western blots. N- and O-specific enzymatic deglycosylation reactions are performed with PNGase F and O-Glycosidase (Bio-Rad), respectively, and the molecular weight of SARG-1 monitored by western blotting. The SARG-1 sequence contains consensus protein kinase C and casein kinase II sites which are known to phosphorylate apoptotic regulators (Verma et al, 2001). The phenotypical differences seen between Trk activation by NGF which leads to PKC activation (Patapoutian et al., 2001) and treatment with the protein kinase inhibitor staurosporine in PC-12 possibly suggesting regulation of SARG-1 function by phosphorylation. To examine possible SARG-1 phosphorylation, immunoprecipitated SARG-1 is probed with polyclonal antibodies against phosphothreonine and phosphoserine in Western blotting analysis and compared to phosphatase-treated protein. Mutant SARG-1 eukaryotic expression plasmids are then generated by site directed mutagenesis to delete potential casein kinase II phosphorylation sites and used to transfect PC-12 cells to monitor the effects of the protein kinase inhibitor staurosporine.

Analysis of Mutation in MS Samples

The immunohistochemical localization of SARG-1 protein to the grey and white matter of the CNS and the role of SARG-1 in apoptotic induction prompted a candidate gene approach to analyse the mutational status of SARG-1 in cases of familial MS. The DNA from twenty unrelated familial multiple sclerosis patients was examined by PCR amplification of the SARG-1 locus and DNA sequencing and compared to SARG-1 sequences from healthy controls. All control samples demonstrated wild type SARG-1 genomic-sequences. From MS patients, only 6 from 20 DNA samples were able to be amplified by PCR. Primer sets used spanned the whole coding region, intron 2/exon 3, and primer pairs specific for exons 1, 2 and 3. Control GAPDH primers were positive for all samples. In 6/20 samples that produced a PCR product, amplificants were TA cloned into the pCR®II vector (Invitrogen) and sequenced. In 4/6 patients, genetic alterations were seen. A T→C point mutation at nucleotide 67 resulting in the substitution of phenylalanine for leucine amino acid 23 (FIG. 16). A C→T point mutation at nucleotide 359 resulting in the substitution of phenylalanine for serine at amino acid 120 (FIG. 17). An A→G point mutation at nucleotide 89 resulting in the substitution of glycine for glutamic acid at amino acid 30 (FIG. 18). Deletion of a codon between amino acids 116 and 121 resulting in the loss of a serine residue (FIG. 19). Sequencing of over 20 control DNA samples revealed only wild type sequence.

Polymorphisms Other Mutations

In sequence analysis of over 30 cancer cell lines, a polymorphism in the human sequence at nucleotide 280 (coding sequence) results in either valine (g residue; shown), methionine (a) or leucine (t) residues at position 94 of the amino acid sequence. In a human melanoma cell line, two mutations in SARG-1 are found: an A→G point mutation at nucleotide 74 resulting in the substitution of aspartic acid for glycine and a C→T point mutation at nucleotide 289 resulting in the substitution of histidine for tyrosine at amino acid 97. Such SARG-1 mutations therefore are suitable markers for human melanomas.

TABLE

| | | | | |
|---|---|---|---|---|
| 67 | T → C | = | F → L | 23 |
| 74 | A → G | = | E → G | 25 |
| 89 | A → G | = | E → G | 30 |
| 289 | C → T | = | H → Y | 97 |
| 359 | C → T | = | S → F | 120 |
| Δ | | | S | 116–121 |

REFERENCE

Bauer et al. (1993), NAR: 21: 4272-4280

Bench et al. (2000), Oncogene 19, 3902-3913

Chataway et al. (1998), Brain 121, 1869-1887

Corset et al. (2000), Nature 407: 747-750

Deloukas et al. (2001), Nature 414; 865-871

Ebers et al. (1995), Nature 377, 150-151

Fraker, in "Cell death", edited by Schwartz et al., Methods in Cell Biology, Vol 46, Academic press, San Diego, Calif. pp57-76
Fu et al. (1999), J. Biol.Chem. 274, 7264-7271
Galiegue et al. (1999), J.Biol.Chem. 274: 2938-2952
Gu et al. (1993), Cell 73: 1155-1164
Haines et al. (1998) Hum.Mol.Genet. 7; 1229-1234
Hashimoto et al. (1989), Exp. Cell Res., 184, 351-359
Jacobson et al. (2000) Nature Genetics, 26, 495-499
Johnson et al. (1995), Gene Probes 2, A Practical Approach, Oxford University Press, chapter 12, 313-327
Kaufman (1992), "The Atlas of Mouse Development" Academic Press, London
Liang et al. (1992), Science; 257: 967-971
Liang et al. (1993), NAR: 21; 3269-3275
Liang et al. (1995), Current opinions in Immunology: 7: 274-280
Lucas et al. (1999), FASEB J. 13, 263-272
Olson et al. (1996), Cell 5: 1-4
Ono et al. (2000), J. Biol.Chem. 275: 31145-31154
Papaioannou et al. (2000) in "Gene Targeting—A Practical Approach" ed. by Joyner
Patapoutia et al. (2001), Curr. Opin. Neurobiol.11: 272-280
Pham et al. (1996), PNAS 93: 13090-13095
Rechsteiner et al. (1996), TIBS 21: 267-271
Rossi et al. (2001), EMBO j. 20: 2844-2856
Sabath et al. (2000), Biotechniques 5: 966-972
Sadovnick et al. (2000), Clin. Genet. 58, 431-435
Sambrock et al. (1989), Molecular cloning a laboratory manual (second edition).
Sawcer et al. (1998), Curr. Opin. Immunol. 10, 697-703
Verma et al. (2001), J. Biol.Chem. 276: 4671-4676
Wattel et al. (1993), Leuk. Res. 17: 921-926
Weinshenker et al. (2000), Neurology, 54, 542-544
White et al. (2000), PNAS 97: 13967-13972
Zipp (2000), Cell Tissue Res. 301, 163-171

The invention claimed is:

1. A method for diagnosing in a patient multiple sclerosis (MS) or the increased risk for acquiring MS, wherein the method comprises the steps of
providing a sample of a body fluid or tissue from the patient; and
testing the sample to determine whether the sample contains a wild type SCF-Apoptosis-Response Gene-1 protein (SARG-1 protein) (SEQ ID NO. 2), whereby the absence of a wild type SARG-1 protein in the sample indicates that the patient has MS or an increased risk of acquiring MS.

2. The method according to claim 1, wherein the sample does not contain a SARG-1 protein.

3. The method according to claim 1, wherein the sample contains a mutant SARG-1 protein.

4. The method according to claim 1, wherein the testing is performed by contacting the sample with an antibody against the wild type SARG-1-protein.

5. A method for diagnosing in a patient multiple sclerosis (MS) or the increased risk for acquiring MS, wherein the method comprises the steps of
providing a sample of a body fluid or tissue from the patient; and
testing the sample to determine whether the sample contains nucleic acid (SEQ ID NO. 1) encoding a wild type SCF-Apoptosis-Response Gene-1 protein (SARG-1 protein) (SEQ ID NO. 2), whereby the absence of a nucleic acid encoding a wild type SARG-1 protein in the sample indicates that the patient has MS or an increased risk of acquiring MS.

6. The method according to claim 5, wherein the sample does not contain a nucleic acid encoding a SARG-1 protein.

7. The method according to claim 5, wherein the sample contains a nucleic acid encoding a mutant SARG-1 protein.

8. The method according to claim 5, wherein the testing is performed by one or more techniques selected from the group consisting of a nucleic acid amplification, polymerase chain reaction (PCR), single-strand conformation polymorphism (SSCP) analysis, restriction analysis, microarray technology and proteomics.

9. The method according to claim 1, wherein the sample is derived from human blood, plasma, serum, lymph, nerve-cell containing tissue, cerebrospinal fluid, all biopsy-material, including tumor tissue, bone marrow, nervous tissue, skin, hair, tears, fetal material, amniocentesis material, uterine tissue, saliva, feces or sperm.

10. The method according to claim 5, wherein the sample is derived from human blood, plasma, serum, lymph, nerve-cell containing tissue, cerebrospinal fluid, all biopsy-material, including tumor tissue, bone marrow, nervous tissue, skin, hair, tears, fetal material, amniocentesis material, uterine tissue, saliva, feces or sperm.

11. The method according to claim 4, wherein the wt-SARG-1-protein antibody is a monoclonal antibody.

* * * * *

SEQUENCE LISTING

```
<160> NUMBER OF SEQ ID NOS: 13

<210> SEQ ID NO 1
<211> LENGTH: 486
<212> TYPE: DNA
<213> ORGANISM: human

<400> SEQUENCE: 1
atggacccaa atcctcgggc cgccctggag cgccagcagc tccgccttcg ggagcggcaa      60
aaattcttcg aggacatttt acagccagag acagagtttg tctttcctct gtcccatctg     120
catctcgagt cgcagagacc ccccataggt agtatctcat ccatggaagt gaatgtggac     180
acactggagc aagtagaact tattgacctt ggggacccgg atgcagcaga tgtgttcttg     240
ccttgcgaag atcctccacc aacccccccag tcgtctgggg tggacaacca tttggaggag     300
ctgagcctgc cggtgcctac atcagacagg accacatcta ggacctcctc ctcctcctcc     360
tccgactcct ccaccaacct gcatagccca aatccaagtg atgatggagc agatacgccc     420
ttggcacagt cggatgaaga ggaggaaagg ggtgatggag gggcagagcc tggagcctgc     480
agctag                                                                486

<210> SEQ ID NO 2
<211> LENGTH: 161
<212> TYPE: PRT
<213> ORGANISM: human

<400> SEQUENCE: 2

Met Asp Pro Asn Pro Arg Ala Ala Leu Glu Arg Gln Gln Leu Arg Leu
 1               5                  10                  15

Arg Glu Arg Gln Lys Phe Phe Glu Asp Ile Leu Gln Pro Glu Thr Glu
            20                  25                  30

Phe Val Phe Pro Leu Ser His Leu His Leu Glu Ser Gln Arg Pro Pro
        35                  40                  45

Ile Gly Ser Ile Ser Ser Met Glu Val Asn Val Asp Thr Leu Glu Gln
    50                  55                  60

Val Glu Leu Ile Asp Leu Gly Asp Pro Asp Ala Ala Asp Val Phe Leu
65                  70                  75                  80

Pro Cys Glu Asp Pro Pro Thr Pro Gln Ser Ser Gly Val Asp Asn
                85                  90                  95
```

```
His Leu Glu Glu Leu Ser Leu Pro Val Pro Thr Ser Asp Arg Thr Thr
                100                 105                 110

Ser Arg Thr Ser Ser Ser Ser Ser Asp Ser Ser Thr Asn Leu His
        115                 120                 125

Ser Pro Asn Pro Ser Asp Asp Gly Ala Asp Thr Pro Leu Ala Gln Ser
    130                 135                 140

Asp Glu Glu Glu Glu Arg Gly Asp Gly Gly Ala Glu Pro Gly Ala Cys
145                 150                 155                 160

Ser

<210> SEQ ID NO 3
<211> LENGTH: 1083
<212> TYPE: DNA
<213> ORGANISM: human

<400> SEQUENCE: 3
ccaggccgga gccaggggcc ccactgttgg gatgctggct gcagtggggc gccccaagcc    60
caggtcccct ctgtcttctc tttcgacttt gcagctgtac ttgttttgct cctctacccg   120
caggagctga catggaccca atcctcgggg ccgccctgga gcgccagcag ctccgccttc   180
gggagcggca aaaattcttc gaggacattt tacagccaga gacagagttt gtctttcctc   240
tgtcccatct gcatctcgag tcgcagagac cccccatagg tagtatctca tccatggaag   300
tgaatgtgga cacactggag caagtagaac ttattgacct ggggacccg gatgcagcag    360 atgtgttctt gccttgcgaa gatcctccac caaccccca gtcgtctggg gtggacaacc    420
atttggagga gctgagcctg ccggtgccta catcagacag gaccacatct aggacctcct   480
cctcctcctc ctccgactcc tccaccaacc tgcatagccc aaatccaagt gatgatggag   540
cagatacgcc cttggcacag tcggatgaag aggaggaaag gggtgatgga ggggcagagc   600
ctggagcctg cagctagcag tgggcccctg cctacagact gaccacgctg gctattctcc   660
acatgagacc acaggcccag ccagagcctg tcgggagaag accagactct ttacttgcag   720
taggcaccag aggtgggaag gatggtggga ttgtgtacct ttctaagaat taaccctctc   780
ctgctttact gctaattttt tcctgctgca accctcccac cagttttggg cttactcctg   840
agatatgatt tgcaaatgag gagagagaag atgaggttgg acaagatgcc actgcttttc   900
ttagcactct tccctccct aaaccatccc gtagtcttct aatacagtct ctcagacaag    960
tgtctctaga tggatgtgaa ctccttaact catcaagtaa ggtggtactc aagccatgct  1020
gcctccttac atccttttg gaacagagca cggtataaat aataaactaa taataatatg  1080
cca                                                                1083

<210> SEQ ID NO 4
<211> LENGTH: 1038
<212> TYPE: DNA
<213> ORGANISM: rat

<400> SEQUENCE: 4
ccagactgga agcgaaggct gtgttgctgg gatgccagct gccgaggggc tgcttaagcc    60
ttggccccca ctactttctg tttcagcccc acttctgtgc gtgtcttact ccattacccc   120
caggggctga catggaccca atcctcgag cagccctgga gcggcagcag ctgcgtctca    180
gggagcggca gaagttcttc gaggacattt tacagccaga gacagagttt gttttccccc   240
tatcccatct gcatctcgag tcacaaagac ccccatagg tagcatctcc tcgatggaag    300
```

-continued

| | | | |
|---|---|---|---|
| tgaatgtgga cacactggag caggtggaat ttattgacct tgcggatcag gatggagcag | 360 |
| atgtgttctt accttgtgag gattctcctc caactcccca gaggtctgga gtggatgacc | 420 |
| acccagagga gctgagcctg ctggtaccca cgtcagacag gaccacatcc cggacctcct | 480 |
| ccttgtcctc tgactcctcc aacctgcgca gtccaaatcc aagtgatggg ggaggagaca | 540 |
| ctcccttggc acagtctgac gaggaggatg gggacggtgg aggggcagaa cctggacctt | 600 |
| gcagctagca gaggcccctt acaaactgag cgatctggct gttctccatg gagaggagac | 660 |
| cttaggtcca ccagagcact ctggagaaga cctgacactt tacttacatc agcaccaaag | 720 |
| ggagggaagg atggtggatg gtgtgcctga gagttagcct ccccgcttta ctgataacgc | 780 |
| tgtcctgctg ccacgccccc acagtgcttt cttctgaggt aggacttcca agtgagactc | 840 |
| tcgaaggtga ggtgggacaa gatgccactg ttttcttact ccctcctgc ccccaaatga | 900 |
| tcctgtagtc tcccactagt ctcctaagcc agtgtctctg agggaaagtt ctgaggagtt | 960 |
| ccactttgca gttatcctgc ctctataagt cctttctggg aacaggatat ggtataaata | 1020 |
| ataaataata ctgtacca | 1038 |

<210> SEQ ID NO 5
<211> LENGTH: 486
<212> TYPE: DNA
<213> ORGANISM: rat

<400> SEQUENCE: 5

| | | |
|---|---|
| atggacccaa atcctcgggc cgccctggag cgccagcagc tccgccttcg ggagcggcaa | 60 |
| aaattcttcg aggacatttt acagccagag acagagtttg tctttcctct gtcccatctg | 120 |
| catctcgagt cgcagagacc ccccataggt agtatctcat ccatggaagt gaatgtggac | 180 |
| acactggagc aagtagaact tattgacctt ggggacccgg atgcagcaga tgtgttcttg | 240 |
| ccttgcgaag atcctccacc aacccccag tcgtctggga tggacaacca tttggaggag | 300 |
| ctgagcctgc cggtgcctac atcagacagg accacatcta ggacctcctc ctcctccttc | 360 |
| tccgactcct ccaccaacct gcatagccca aatccaagtg atgatggagc agatacgccc | 420 |
| ttggcacagt cggatgaaga ggaggaaagg ggtgatggag gggcagagcc tggagcctgc | 480 |
| agctag | 486 |

<210> SEQ ID NO 6
<211> LENGTH: 158
<212> TYPE: PRT
<213> ORGANISM: rat

<400> SEQUENCE: 6

Met Asp Pro Asn Pro Arg Ala Ala Leu Glu Arg Gln Gln Leu Arg Leu
1               5                   10                  15

Arg Glu Arg Gln Lys Phe Phe Glu Asp Ile Leu Gln Pro Glu Thr Glu
            20                  25                  30

Phe Val Phe Pro Leu Ser His Leu His Leu Glu Ser Gln Arg Pro Pro
        35                  40                  45

Ile Gly Ser Ile Ser Ser Met Glu Val Asn Val Asp Thr Leu Glu Gln
    50                  55                  60

Val Glu Phe Ile Asp Leu Ala Asp Gln Asp Gly Ala Asp Val Phe Leu
65                  70                  75                  80

Pro Cys Glu Asp Ser Pro Pro Thr Pro Gln Arg Ser Gly Val Asp Asp
                85                  90                  95

His Pro Glu Glu Leu Ser Leu Leu Val Pro Thr Ser Asp Arg Thr Thr

```
            100                 105                 110
Ser Arg Thr Ser Ser Leu Ser Ser Asp Ser Ser Asn Leu Arg Ser Pro
        115                 120                 125

Asn Pro Ser Asp Gly Gly Gly Asp Thr Pro Leu Ala Gln Ser Asp Glu
    130                 135                 140

Glu Asp Gly Asp Gly Gly Ala Glu Pro Gly Pro Cys Ser
145                 150                 155

<210> SEQ ID NO 7
<211> LENGTH: 1002
<212> TYPE: DNA
<213> ORGANISM: mouse

<400> SEQUENCE: 7
ggatccaacg ccggcgctgc tcgctcccac gcccccgccg ccgcttgtcg ggagcgcacc      60
cagggagcca gcggggcgcg ggcgctgcag gggctgacat ggacccaaat ccgagagcag     120
ccctggagcg ccaacagctg cggctccggg agaggcagaa gttctttgag acatttttac     180
agccagagac agagtttgtc ttcccccctgt cccatctgca cctggagtca aaagacccc     240 ccataggtag catctcgtct atggaagtga atgtggacac actggagcaa gtggagttta     300
ttgatcttgc ggatcaggat ggagcagatg tgttcttgcc ttgtgaggag tcctcgccag     360 ctcccccagat gtctggagtg gatgaccatc agaggagct gagcctgctg gtacccacgt     420
ctgacaggac cacatcccgg acctcctcct tgtcctctga ctcctccaac ctgcgcagtc     480
caaatccaag tgatggggga ggagacactc ccttggcaca gtctgatgag gaggacgggg     540
atgacggagg ggcagagcct ggaccctgca gctagcagtg ggcctcgtac agactgacca     600
gcccggctgt tctccatgga aaggagacct aggcccagca gagcctggag aagacctgac     660
actttcctta cttcagcacc aaagggaggg aaggatggtg gatggtgtgc ctgagagtta     720
gcctcccctg ctttaccgta acgctatcct gctgccacgc ccccacagtg cttttcttct     780
gaggtaggac ttccaagtga acttgagag gtgaggtggg acaagacgca gctgctttct     840
tagtcccctc ctgcccccag atgatcctgt tgtcttccac agagtctcct aagccagtgt     900
ctctgagggg atgttctgag gagttccact ttccagttat cctgcctcta taagttcttt     960
tgggaacagg atatggtata aataataaat aataatatac ca                      1002

<210> SEQ ID NO 8
<211> LENGTH: 477
<212> TYPE: DNA
<213> ORGANISM: mouse

<400> SEQUENCE: 8
atggacccaa atccgagagc agccctggag cgccaacagc tgcggctccg ggagaggcag      60
aagttctttg aggacatttt tacagccaga gacagagtttg tcttcccccct gtcccatctg     120 cacctggagt cacaaagacc cccataggt agcatctcgt ctatggaagt gaatgtggac     180
acactggagc aagtggagtt tattgatctt gcggatcagg atggagcaga tgtgttcttg     240
ccttgtgagg agtcctcgcc agctccccag atgtctggag tggatgacca tcagaggag     300 ctgagcctgc tggtacccac gtctgacagg accacatccc ggacctcctc cttgtcctct     360
gactcctcca acctgcgcag tccaaatcca agtgatgggg gaggagacac tcccttggca     420
cagtctgatg aggaggacgg ggatgacgga ggggcagagc ctggaccctg cagctag       477

<210> SEQ ID NO 9
```

```
<211> LENGTH: 158
<212> TYPE: PRT
<213> ORGANISM: mouse

<400> SEQUENCE: 9

Met Asp Pro Asn Pro Arg Ala Ala Leu Glu Arg Gln Gln Leu Arg Leu
 1               5                  10                  15

Arg Glu Arg Gln Lys Phe Phe Glu Asp Ile Leu Gln Pro Glu Thr Glu
             20                  25                  30

Phe Val Phe Pro Leu Ser His Leu His Leu Glu Ser Gln Arg Pro Pro
         35                  40                  45

Ile Gly Ser Ile Ser Ser Met Glu Val Asn Val Asp Thr Leu Glu Gln
     50                  55                  60

Val Glu Phe Ile Asp Leu Ala Asp Gln Asp Gly Ala Asp Val Phe Leu
 65                  70                  75                  80

Pro Cys Glu Glu Ser Ser Pro Ala Pro Gln Met Ser Gly Val Asp Asp
                 85                  90                  95

His Pro Glu Glu Leu Ser Leu Leu Val Pro Thr Ser Asp Arg Thr Thr
            100                 105                 110

Ser Arg Thr Ser Ser Leu Ser Ser Asp Ser Ser Asn Leu Arg Ser Pro
        115                 120                 125

Asn Pro Ser Asp Gly Gly Gly Asp Thr Pro Leu Ala Gln Ser Asp Glu
    130                 135                 140

Glu Asp Gly Asp Asp Gly Gly Ala Glu Pro Gly Pro Cys Ser
145                 150                 155

<210> SEQ ID NO 10
<211> LENGTH: 161
<212> TYPE: PRT
<213> ORGANISM: human

<400> SEQUENCE: 10

Met Asp Pro Asn Pro Arg Ala Ala Leu Glu Arg Gln Gln Leu Arg Leu
 1               5                  10                  15

Arg Glu Arg Gln Lys Phe Leu Glu Asp Ile Leu Gln Pro Glu Thr Glu
             20                  25                  30

Phe Val Phe Pro Leu Ser His Leu His Leu Glu Ser Gln Arg Pro Pro
         35                  40                  45

Ile Gly Ser Ile Ser Ser Met Glu Val Asn Val Asp Thr Leu Glu Gln
     50                  55                  60

Val Glu Leu Ile Asp Leu Gly Asp Pro Asp Ala Ala Asp Val Phe Leu
 65                  70                  75                  80

Pro Cys Glu Asp Pro Pro Thr Pro Gln Ser Ser Gly Val Asp Asn
                 85                  90                  95

His Leu Glu Glu Leu Ser Leu Pro Val Pro Thr Ser Asp Arg Thr Thr
            100                 105                 110

Ser Arg Thr Ser Ser Ser Ser Asp Ser Ser Thr Asn Leu His
        115                 120                 125

Ser Pro Asn Pro Ser Asp Gly Ala Asp Thr Pro Leu Ala Gln Ser
    130                 135                 140

Asp Glu Glu Glu Glu Arg Gly Asp Gly Ala Glu Pro Gly Ala Cys
145                 150                 155                 160

Ser

<210> SEQ ID NO 11
<211> LENGTH: 161
```

```
<212> TYPE: PRT
<213> ORGANISM: human

<400> SEQUENCE: 11

Met Asp Pro Asn Pro Arg Ala Ala Leu Glu Arg Gln Gln Leu Arg Leu
  1               5                  10                  15

Arg Glu Arg Gln Lys Phe Phe Glu Asp Ile Leu Gln Pro Glu Thr Glu
             20                  25                  30

Phe Val Phe Pro Leu Ser His Leu His Leu Glu Ser Gln Arg Pro Pro
         35                  40                  45

Ile Gly Ser Ile Ser Ser Met Glu Val Asn Val Asp Thr Leu Glu Gln
 50                  55                  60

Val Glu Leu Ile Asp Leu Gly Asp Pro Asp Ala Ala Asp Val Phe Leu
 65                  70                  75                  80

Pro Cys Glu Asp Pro Pro Thr Pro Gln Ser Ser Gly Val Asp Asn
                 85                  90                  95

His Leu Glu Glu Leu Ser Leu Pro Val Pro Thr Ser Asp Arg Thr Thr
             100                 105                 110

Ser Arg Thr Ser Ser Ser Phe Ser Asp Ser Thr Asn Leu His
         115                 120                 125

Ser Pro Asn Pro Ser Asp Asp Gly Ala Asp Thr Pro Leu Ala Gln Ser
         130                 135                 140

Asp Glu Glu Glu Glu Arg Gly Asp Gly Gly Ala Glu Pro Gly Ala Cys
145                 150                 155                 160

Ser

<210> SEQ ID NO 12
<211> LENGTH: 161
<212> TYPE: PRT
<213> ORGANISM: human

<400> SEQUENCE: 12

Met Asp Pro Asn Pro Arg Ala Ala Leu Glu Arg Gln Gln Leu Arg Leu
  1               5                  10                  15

Arg Glu Arg Gln Lys Phe Phe Glu Asp Ile Leu Gln Pro Gly Thr Glu
             20                  25                  30

Phe Val Phe Pro Leu Ser His Leu His Leu Glu Ser Gln Arg Pro Pro
         35                  40                  45

Ile Gly Ser Ile Ser Ser Met Glu Val Asn Val Asp Thr Leu Glu Gln
 50                  55                  60

Val Glu Leu Ile Asp Leu Gly Asp Pro Asp Ala Ala Asp Val Phe Leu
 65                  70                  75                  80

Pro Cys Glu Asp Pro Pro Thr Pro Gln Ser Ser Gly Val Asp Asn
                 85                  90                  95

His Leu Glu Glu Leu Ser Leu Pro Val Pro Thr Ser Asp Arg Thr Thr
             100                 105                 110

Ser Arg Thr Ser Ser Ser Ser Asp Ser Thr Asn Leu His
         115                 120                 125

Ser Pro Asn Pro Ser Asp Asp Gly Ala Asp Thr Pro Leu Ala Gln Ser
         130                 135                 140

Asp Glu Glu Glu Glu Arg Gly Asp Gly Gly Ala Glu Pro Gly Ala Cys
145                 150                 155                 160

Ser
```

```
<210> SEQ ID NO 13
<211> LENGTH: 160
<212> TYPE: PRT
<213> ORGANISM: human

<400> SEQUENCE: 13

Met Asp Pro Asn Pro Arg Ala Ala Leu Glu Arg Gln Gln Leu Arg Leu
1               5                   10                  15

Arg Glu Arg Gln Lys Phe Phe Glu Asp Ile Leu Gln Pro Glu Thr Glu
            20                  25                  30

Phe Val Phe Pro Leu Ser His Leu His Leu Glu Ser Gln Arg Pro Pro
        35                  40                  45

Ile Gly Ser Ile Ser Ser Met Glu Val Asn Val Asp Thr Leu Glu Gln
    50                  55                  60

Val Glu Leu Ile Asp Leu Gly Asp Pro Asp Ala Ala Asp Val Phe Leu
65                  70                  75                  80

Pro Cys Glu Asp Pro Pro Thr Pro Gln Ser Ser Gly Val Asp Asn
                85                  90                  95

His Leu Glu Glu Leu Ser Leu Pro Val Pro Thr Ser Asp Arg Thr Thr
            100                 105                 110

Ser Arg Thr Ser Ser Ser Ser Ser Asp Ser Ser Thr Asn Leu His Ser
        115                 120                 125

Pro Asn Pro Ser Asp Asp Gly Ala Asp Thr Pro Leu Ala Gln Ser Asp
    130                 135                 140

Glu Glu Glu Glu Arg Gly Asp Gly Gly Ala Glu Pro Gly Ala Cys Ser
145                 150                 155                 160
```